(12) United States Patent
Uhrich et al.

(10) Patent No.: US 10,543,162 B2
(45) Date of Patent: Jan. 28, 2020

(54) KOJIC ACID POLYMERS

(71) Applicant: Rutgers, The State University of New Jersey, New Brunswick, NJ (US)

(72) Inventors: Kathryn Uhrich, New Brunswick, NJ (US); Kervin Smith, New Brunswick, NJ (US); Jonathan Faig, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 15/565,313

(22) PCT Filed: Apr. 11, 2016

(86) PCT No.: PCT/US2016/026931
§ 371 (c)(1),
(2) Date: Oct. 9, 2017

(87) PCT Pub. No.: WO2016/164898
PCT Pub. Date: Oct. 13, 2016

(65) Prior Publication Data
US 2018/0116945 A1 May 3, 2018

Related U.S. Application Data

(60) Provisional application No. 62/146,027, filed on Apr. 10, 2015.

(51) Int. Cl.
*A61K 8/85* (2006.01)
*A61K 31/351* (2006.01)
(Continued)

(52) U.S. Cl.
CPC ............... *A61K 8/85* (2013.01); *A61K 8/498* (2013.01); *A61K 9/0014* (2013.01);
(Continued)

(58) Field of Classification Search
CPC ........ A61K 8/498; A61K 8/85; A61K 47/593; A61K 9/0014; A61K 31/351; A61Q 19/02; A61P 17/00
See application file for complete search history.

(56) References Cited

U.S. PATENT DOCUMENTS 2,607,799 A   8/1952 Weesner
2,986,553 A   5/1961 McCulloch
(Continued)

FOREIGN PATENT DOCUMENTS

AU       750424      3/2003
CA      2393676      7/2002
(Continued)

OTHER PUBLICATIONS

Ibim, "Preliminary in vivo report on the osteocompatibility of poly(anhydride-co-imides) evaluated in a tibial model", Journal of Biomedical Material Research, 43(4), 374-379, (Winter 1998).
(Continued)

*Primary Examiner* — Jianfeng Song
(74) *Attorney, Agent, or Firm* — Viksnins Harris Padys Malen LLP

(57) ABSTRACT

A controlled release system for kojic acid having improved stability has been identified. To minimize degradation, kojic acid was incorporated into a hydrolytically degradable polymer (e.g., a polycarbonate-ester)). By synthesizing polymer precursors containing kojic acid-linker-kojic acid chemical structures, versatile monomers were developed that can be used to modulate polymer properties. Additionally the synthetic method lends itself to the development of other polymer systems. Polymers having one or more groups that will yield kojic acid upon degradation of the polymer backbone, as well as methods of use thereof are described.

16 Claims, 6 Drawing Sheets

(51) Int. Cl.
  *A61K 47/59* (2017.01)
  *A61K 8/49* (2006.01)
  *A61K 9/00* (2006.01)
  *A61P 17/00* (2006.01)
  *A61Q 19/02* (2006.01)
  *C08G 64/06* (2006.01)

(52) U.S. Cl.
  CPC .......... *A61K 31/351* (2013.01); *A61K 47/593* (2017.08); *A61P 17/00* (2018.01); *A61Q 19/02* (2013.01); *C08G 64/06* (2013.01)

(56) References Cited

U.S. PATENT DOCUMENTS

| | | |
|---|---|---|
| 4,062,855 A | 12/1977 | Allan et al. |
| 4,126,445 A | 11/1978 | Allan et al. |
| 4,164,560 A | 8/1979 | Folkman et al. |
| 4,298,595 A | 11/1981 | Parkinson et al. |
| 4,375,968 A | 3/1983 | Manhart et al. |
| 4,414,203 A | 11/1983 | Cabardo, Jr. et al. |
| 4,591,496 A | 5/1986 | Cohen et al. |
| 4,612,302 A | 9/1986 | Szabo et al. |
| 4,684,620 A | 8/1987 | Hruby et al. |
| 4,757,128 A | 7/1988 | Domb et al. |
| 4,792,598 A | 12/1988 | Ziegast |
| 4,857,311 A | 8/1989 | Domb et al. |
| 4,868,274 A | 9/1989 | Gupta et al. |
| 4,886,870 A | 12/1989 | D'Amore et al. |
| 4,888,176 A | 12/1989 | Langer et al. |
| 4,891,225 A | 1/1990 | Langer et al. |
| 4,906,474 A | 3/1990 | Langer et al. |
| 4,916,204 A | 4/1990 | Domb et al. |
| 4,938,949 A | 7/1990 | Borch et al. |
| 4,997,904 A | 3/1991 | Domb |
| 4,999,417 A | 3/1991 | Domb |
| 5,032,216 A | 7/1991 | Felten |
| 5,082,925 A | 1/1992 | Shalaby et al. |
| 5,160,745 A | 11/1992 | Deluca et al. |
| 5,175,235 A | 12/1992 | Domb et al. |
| 5,259,968 A | 11/1993 | Emert et al. |
| 5,264,540 A | 11/1993 | Cooper et al. |
| 5,290,494 A | 3/1994 | Coombes et al. |
| 5,317,079 A | 5/1994 | Domb et al. |
| 5,364,725 A | 11/1994 | Wilson et al. |
| 5,498,729 A | 3/1996 | Domb |
| 5,512,131 A | 4/1996 | Kumar et al. |
| 5,514,764 A | 5/1996 | Frechet et al. |
| 5,518,730 A | 5/1996 | Fuisz |
| 5,545,409 A | 8/1996 | Laurencin et al. |
| 5,629,009 A | 5/1997 | Laurencin et al. |
| 5,660,851 A | 8/1997 | Domb |
| 5,721,131 A | 2/1998 | Rudolph et al. |
| 5,776,748 A | 7/1998 | Singhvi et al. |
| 5,798,115 A | 8/1998 | Santerre et al. |
| 5,837,278 A | 11/1998 | Geistlich et al. |
| 5,889,028 A | 3/1999 | Sandborn et al. |
| 5,891,477 A | 4/1999 | Lanza et al. |
| 5,902,110 A | 5/1999 | Alfano et al. |
| 5,902,599 A | 5/1999 | Anseth et al. |
| 5,916,585 A | 6/1999 | Cook et al. |
| 5,937,758 A | 8/1999 | Maracas et al. |
| 5,942,252 A | 8/1999 | Tice et al. |
| 5,958,911 A | 9/1999 | Evans et al. |
| 5,969,020 A | 10/1999 | Shalaby et al. |
| 6,071,530 A | 6/2000 | Polson et al. |
| 6,123,956 A | 9/2000 | Baker et al. |
| 6,153,212 A | 11/2000 | Mao et al. |
| 6,171,610 B1 | 1/2001 | Vacanti et al. |
| 6,280,772 B1 | 8/2001 | Pinkus |
| 6,365,149 B2 | 4/2002 | Vyakarnam et al. |
| 6,468,519 B1 | 10/2002 | Uhrich |
| 6,486,214 B1 | 11/2002 | Uhrich |
| 6,602,915 B2 | 8/2003 | Uhrich |
| 6,613,807 B2 | 9/2003 | Uhrich |
| 6,685,928 B2 | 2/2004 | Uhrich et al. |
| 6,689,350 B2 | 2/2004 | Uhrich |
| 7,122,615 B1 | 10/2006 | Uhrich |
| 7,396,527 B2 | 7/2008 | Uhrich |
| 7,411,031 B2 | 8/2008 | Uhrich et al. |
| 7,534,852 B2 | 5/2009 | Uhrich |
| 7,662,864 B2 | 2/2010 | Kanamathareddy et al. |
| 7,666,398 B2 | 2/2010 | Uhrich |
| 7,985,415 B2 | 7/2011 | Giroux |
| 8,017,714 B2 | 9/2011 | Uhrich |
| 8,088,405 B2 | 1/2012 | Uhrich et al. |
| 8,221,790 B2 | 7/2012 | Uhrich |
| 8,232,322 B2 | 7/2012 | East et al. |
| 8,241,668 B2 | 8/2012 | Uhrich et al. |
| 8,263,060 B2 | 9/2012 | Uhrich et al. |
| 8,361,453 B2 | 1/2013 | Uhrich et al. |
| 8,741,317 B2 | 6/2014 | Uhrich et al. |
| 8,747,832 B2 | 6/2014 | Uhrich et al. |
| 9,108,070 B2 | 8/2015 | Kanamathareddy et al. |
| 9,144,579 B2 | 9/2015 | Uhrich et al. |
| 9,387,250 B2 | 7/2016 | Uhrich et al. |
| 9,782,432 B2 | 10/2017 | Uhrich et al. |
| 9,862,672 B2 | 1/2018 | Uhrich et al. |
| 10,023,521 B2 | 7/2018 | Uhrich et al. |
| 10,092,578 B2 | 10/2018 | Kanamathareddy et al. |
| 2003/0035787 A1 | 2/2003 | Uhrich et al. |
| 2003/0059469 A1 | 3/2003 | Uhrich et al. |
| 2004/0038948 A1 | 2/2004 | Uhrich et al. |
| 2004/0044125 A1 | 3/2004 | Uhrich et al. |
| 2004/0096476 A1 | 5/2004 | Uhrich et al. |
| 2004/0198641 A1 | 10/2004 | Uhrich et al. |
| 2004/0228832 A1 | 11/2004 | Uhrich et al. |
| 2005/0031577 A1 | 2/2005 | Uhrich et al. |
| 2005/0053577 A1 | 3/2005 | Uhrich et al. |
| 2005/0089504 A1 | 4/2005 | Uhrich et al. |
| 2005/0089506 A1 | 4/2005 | Uhrich et al. |
| 2005/0100526 A1 | 5/2005 | Uhrich et al. |
| 2005/0131199 A1 | 6/2005 | Uhrich et al. |
| 2005/0249697 A1 | 11/2005 | Uhrich et al. |
| 2006/0013851 A1 | 1/2006 | Giroux et al. |
| 2006/0039964 A1 | 2/2006 | Uhrich et al. |
| 2006/0057179 A1 | 3/2006 | Giroux et al. |
| 2006/0188546 A1 | 8/2006 | Giroux |
| 2007/0014832 A1 | 1/2007 | Uhrich |
| 2007/0098800 A1 | 5/2007 | Giroux et al. |
| 2007/0196417 A1 | 8/2007 | Uhrich et al. |
| 2008/0226583 A1 | 9/2008 | Uhrich |
| 2008/0233078 A1 | 9/2008 | Uhrich |
| 2009/0035248 A1 | 2/2009 | Uhrich et al. |
| 2010/0074937 A1 | 3/2010 | Uhrich |
| 2010/0152410 A1 | 6/2010 | East et al. |
| 2010/0291180 A1 | 11/2010 | Uhrich et al. |
| 2010/0291181 A1 | 11/2010 | Uhrich et al. |
| 2010/0310498 A1 | 12/2010 | Kanamathareddy et al. |
| 2011/0022161 A1 | 1/2011 | Uhrich et al. |
| 2013/0022569 A1 | 1/2013 | Uhrich et al. |
| 2013/0071458 A1 | 3/2013 | Kanamathareddy et al. |
| 2014/0030341 A1 | 1/2014 | Uhrich et al. |
| 2014/0050692 A1 | 2/2014 | Uhrich et al. |
| 2014/0120057 A1 | 5/2014 | Uhrich et al. |
| 2016/0058776 A1 | 3/2016 | Kanamathareddy et al. |

FOREIGN PATENT DOCUMENTS

| | | |
|---|---|---|
| DE | 288311 | 3/1991 |
| DE | 0288387 | 3/1991 |
| EP | 0246341 | 11/1987 |
| EP | 0483429 | 5/1992 |
| EP | 0498283 | 8/1992 |
| EP | 0580386 | 1/1994 |
| JP | 51134729 | 11/1976 |
| JP | 53082743 | 7/1978 |
| JP | 56007716 | 1/1981 |
| JP | 6255797 | 12/1985 |
| JP | 61186309 | 8/1986 |
| JP | H05310727 | 11/1993 |
| JP | 06328857 | 11/1994 |
| JP | 07149044 | 6/1995 |
| JP | H08245722 | 9/1996 |
| NL | 9000237 | 8/1991 |

(56) References Cited

FOREIGN PATENT DOCUMENTS

| WO | 199009779 | 9/1990 | | |
|---|---|---|---|---|
| WO | 199109831 | 7/1991 | | |
| WO | 199118940 | 12/1991 | | |
| WO | 199739738 | 10/1997 | | |
| WO | 199744016 | 11/1997 | | |
| WO | 199749385 | 12/1997 | | |
| WO | 199836013 | 8/1998 | | |
| WO | 1999012990 | 3/1999 | | |
| WO | 199929885 | 6/1999 | | |
| WO | 199936107 | 7/1999 | | |
| WO | 200066730 | 11/2000 | | |
| WO | 2001028492 | 4/2001 | | |
| WO | 2001041753 | 6/2001 | | |
| WO | 2002009767 | 2/2002 | | |
| WO | 2002009768 | 2/2002 | | |
| WO | 2002009769 | 2/2002 | | |
| WO | WO-02053562 A1 * | 7/2002 | ........... | C07D 309/38 |
| WO | 2003046034 | 6/2003 | | |
| WO | 2003065928 | 8/2003 | | |
| WO | 2003066053 | 8/2003 | | |
| WO | 2003072020 | 9/2003 | | |
| WO | 2004006863 | 1/2004 | | |
| WO | 2004039355 | 5/2004 | | |
| WO | 2004045549 | 6/2004 | | |
| WO | 2005039489 | 5/2005 | | |
| WO | 2005042600 | 5/2005 | | |
| WO | 2006127667 | 11/2006 | | |
| WO | 2007143698 | 12/2007 | | |
| WO | 2008034019 | 3/2008 | | |
| WO | 2008103744 | 8/2008 | | |
| WO | 2008128193 | 10/2008 | | |
| WO | 2009026544 | 2/2009 | | |
| WO | 2012139015 | 10/2012 | | |
| WO | 2014194055 | 12/2014 | | |
| WO | 2015191742 | 12/2015 | | |

OTHER PUBLICATIONS

Ito, "Micropatterned immobilization of epidermal growth factor to regulate cell function", Bioconjugate Chemistry, 9(2), 277-82, (Mar.-Apr. 1998).
James, "Patterned Protein Layers on Solid Substrates by Thin Stamp Microcontact Printing", Langmuir, 14(4), 741-744, (1998).
Jeffcoat, "The Effect of Systemic Flurbiprofen on Bone Supporting Dental Implants", Journal of American Dental Associate, 126, 305-311 (1995).
Jiang, "Synthesis, Characterization and In Vitro Degradation of a New Family of Alternate Poly(ester-anhydrides) Based on Aliphatic and Aromatic Diacids", Biomaterials, 22(3), 211-218, (2001).
Jucker, et al., "Fetal rat septals cells adhere to and extend processes on basement membrane, laminin, and a synthetic peptide from the laminin a chain sequence", Journal of Neuroscience Research, 28(4), 507-17, (Apr. 1991).
Kleinfeld, "Controlled outgrowth of dissociated neurons on patterned substrates", Journal of Neuroscience, 8(11), 1098-120, (Nov. 1998).
Krogh-Jespersen, "Synthesis of a Novel Aromatic Polyanhydride Containing Aminosalicylic Acid", Polymer Preprints, 41(1), 1048-1049, (2000).
Langer, "New Methods of Drug Delivery", Science, 249(4976), 1527-1533, (Sep. 1990).
Laurencin, "Poly(anhydrides-co-imides): In Vivo Biocompatibility Study", 23rd Annual Meeting of the Society for Biomaterials, New Orleans, LA, 483, (1997).
Laurencin, "The Biocompatibility of Poly(anhydride-co-imides): High Strength Polymers for Controlled Drug Delivery", Proc. 24th Int'l Symp. Control. Rel. Bioact. Mater, 973-974, (1997).
Laurencin, "The Bone Biocompatibility of Poly(anhydride-co-imides)—A new generation degradable Polymer for Orthopedic Applications", 41st Annual Meeting of the Orthopedic Research Society, Orlando, FL, 143-24, (1995).

Laurencin, et al., "The controlled delivery of radiosensitizers: taxol treatment for Ewing Sarcoma", Proceedings of the 25th Int'l Symp. Control. Rel. Bioact. Mater., pp. 236-237, (1998).
Longer, "Sustained-Release Drug Delivery Systems", Remington's Pharmaceutical Sciences, 18th Edition, Chapter 91, 1676-1693, (1990).
Macedo, et al., "The in vivo Response to a Bioactive Biodegradable Polymer", Journal of Dental Research, 78, Abstract No. 2827, 459, (1999).
Macedo, "The In Vivo Response to Bioactive Polyanhydride Monofilament", Journal of Dental Research, 79 (Abstract No. 3872), 627, (2000).
March, Advanced organic chemistry: reactions, mechanisms, and structure, 4th Edition, New York: Willey, 419-437 (1992).
Patent Cooperation Treaty, International Searching Authority, Search Report and Written Opinion for PCT/US2016/026931, 10 pages, dated Jul. 1, 2016.
Pinther, "Synthesis of Polyanhydrides Containing Ester Groups", Die Makromolekulare Chemie, Rapid Communications, 11(8), 403-408, (Aug. 1990).
Reynolds, et al., "Non-steroidal anti-inflammatory drug (NSAID)-derived poly(anhydride-esters) in bone and periodontal regeneration", Current Drug Delivery, 4(3), 233-239 (Jan. 1, 2007).
Schacht, "Polymers for Colon Specific Drug Delivery", Journal of Controlled Release, 39, 327-338, (1996).
Schmalenberg, "Microlithographic patterning of polymer substrates for directed neuronal", Polymeric Materials Science Engineering, 81, Fall Meeting, Aug. 22-26, 1999, New Orleans, LA., 97, (1999).
Schmalenberg, "Patterned Polymer Substrates for directing Neuronal Growth", ACS Regional Mid-Atlantic Research Meeting, (1999).
Schmalenberg, "Patterning of polymer substrates for directed neuronal growth studies", Laboratory for Surface Modification,(Mar. 18, 1999).
Schmalenberg, "Thin Stamp Microcontact Patterned Printing of Protein Layers on Polymer Substrates", Transactions: Twenty-Fifth Annual Meeting of the Society for Biomaterials, Apr. 28-May 2, 1999.
Seidel, "Erosion of Poly(anhydride-co-imides): A Preliminary Mechanistic Study", J. Appl. Polym. Sci., 62(8), 1277-1283, (1996).
Shen, "Morphological Characterization of Erodible Polymer Carriers for Drug Release", Proc. 26th Int'l Symp. Control. Rel. Bioact. Mater., 717-718, (1999).
Smith, et al., "Synthesis of Kojic Acid Based Poly(carbonate-esters)", (poster) Celebration of Undergraduate Achievement, Department of Chemistry and Chemical Biology, Rutgers University; Apr. 10, 2015.
Spargo, et al., "Spatially controlled adhesion, spreading, and differentiation of endothelial cells on self-assembled molecular monolayers", Proceedings of the National Academy of Science USA,91(23), 11070-11074, (Nov. 8, 1994).
St. John, "Diffraction-based cell detection using a microcontact printed antibody grating", Analytical Chemistry, 70(6), 1108-11, (Mar. 15, 1998).
Swinyard, "Pharmaceutical Necessities", In: Remington's pharmaceutical sciences by Joseph P. Remington; Alfonso R. Gennaro, Easton, PA.: Mack Pub. Co.: ISBN: 0912734043, 1286-1329 (1990).
Tashiro, et al., "A synthetic peptide containing the IKVAV sequence from the a chain of laminin mediates cell attachment, migration, and neurite outgrowth", Journal of Biological Chemistry, 264(27), 16174-82, (Sep. 25, 1989).
The Merck Index, Twelfth Edition, Merck & Co., Inc. Ed. By S. Budavari et al., p. 1090, compound 6435 (1996).
Uhrich, "Chemical Changes during in vivo degradation of poly(anhydride-imide) matrices", Biomaterials, 19(22), 2045-2050, (1998).
Uhrich, "Degradation of poly(anhydride-co-imides): Novel Polymers for Orthopedic Applications", Mat. Res. Soc. Symp. Proc., 394, 41-46, (1995).
Uhrich, "In Vitro Degradation Characteristics of Poly(anhydride-imides) Containing Pyromellitylimidoalanine", J. Appl. Polymer Sci., Part A, Polym. Chem., 34(7), 1261-1269, (1996).

(56) References Cited

OTHER PUBLICATIONS

Uhrich, "In Vitro Degradation Characteristics of Poly(anhydride-imides) Containing trimellitylimidoglycine", J. Appl. Polymer Sci., 63(11), 1401-1411, (1997).
Uhrich, "Poly(anhydride-ester) Degradation: Mechanical Changes and Correlation to Antibiotic Release", American Chemical Society, Abstracts of Papers, Part 2, Abstract No. 121, 221st ACS National Meeting, San Diego, CA, Abstract 121, (2001).
Uhrich, "Synthesis and Characterization of Degradable poly(anhydride-co-imides)", Macromolecules, 28(7), 2184-2193, (1995).
Uhrich, "Synthesis and Characterization of poly(anhydride co-imides): Solution Polycondensation of Biodegradable Polymers Derived from Amino Acids", Proc. of the American Chemical Society, Division of Polymeric Materials: Science and Engineering, 70, Spring Meeting, San Diego, CA, 239-240, (1994).
Uhrich, "Synthesis of Aminosalicylate-based polyanhydride Prodrugs: Esters, Amides, and Azos", American Chemical Society, Abstracts of Papers, Part 2, Abstract No. 407, 222nd ACS National Meeting, Chicago, IL, Abstract 407, (2001).
Woo, "Biological Characterization of a Novel Biodegradable Antimicrobial Polymer Synthesized with Fluoroquinolones", J. Biomed. Mater. Res. 59, 35-45, (2002).
Woo, et al., "Synthesis and characterization of a novel biodegradable antimicrobial polymer", Biomaterials, 21, 1235-1246 (2000).
Yazdi, et al., "Effects of non-steroidal anti-inflammatory drugs on demineralized bone-induced bone formation", Journal of Periodontal Research, 27(1), 28-33, (Jan. 1992).
Yoda, "Synthesis of polyanhydrides. XII. Crystalline and high melting polyamidepolyanhydride of methylenebis(p-carboxybhenypamide", Journal of Polymer Science, 1, 1323-1338, (1963).
Zaugg, et al., "Modification of Hemoglobin with Analogs of Aspirin", The Journal of Biological Chemistry, 255(7), 2816-2821, (1980).
Aebischer, et al., "Basic fibroblast growth factor released from synthetic guidance channels facilitates peripheral nerve regeneration across long nerve gaps", Journal of Neuroscience Research, 23(3), 282-289, (Jul. 1989).
Anastasiou, "Novel Polyanhydrides with Enhanced Thermal and Solubility Properties", Macromolecules, 33(17), 6217-6221, (2000).
Anastasiou, "Novel, Degradable Polyanhydrides", 25th Annual Meeting Transactions of the Society for Biomaterials, Abstract, 79, (1999).
Anastasiou, "Synthesis of Novel, Degradable Polyanhydrides Containing Para-Aminosalicylic Acid as Drug Delivery Devices for Tuberculosis Treatment", Polymer Preprints, 41(2), 1366-1367, (Aug. 2000).
Ando, et al., "Quasi-Drugs Developed in Japan for the Prevention or Treatment of Hyperpigmentary Disorders", Int J Mol Sci 11(6), 2566-2575 (2010).
Attawia, "Biocompatibility Testing of Poly(anhydride-co-imides) Containing Pyromellitylimidoalanine", The 21st Annual Meeting of the Society for Biomaterials, Abstract, 222, (Apr. 5 -9, 1994).
Attawia, "Cytotoxicity testing of poly(anhydride-co-imides) for orthopedic applications", Journal of Biomedical Materials Research, 29(10), 1233-1240, (1995).
Attawia, "In vitro bone biocompatibility of poly(anhydride-co-imides) containing pyromellitylimidoalanine", Journal of Orthopedic Research, 14(3), 445-454, (1996).
Attawia, "Proliferation, Morphology, and Protein Expression by Osteoblasts Cultured on Poly(anhydride-co-amides)", Journal of Biomedical Materials Research, 48(3), 322-327, (1999).
Attawia, "Regional drug delivery with radiation for the treatment of Ewing's sarcoma—in vitro development of a taxol release system", Journal of Controlled Release, 71, 193-202 (2001).
Attawia, "The Long Term Osteoblast Response to Poly(anhydride-co-imides): A New Degradable Polymer for Use in Bone", Proceedings of the Fifth World Biomaterials Congress, Toronto, Canada, 113, (1996).

Beaton, "Synthesis of a novel poly(anhydride-ester)", The Rutgers Scholar—An Electronic Bulletin of Undergraduate Research, 3, 1-7, (2001), http://www.scils.rutgers.edu/~weyang/ejournal/volume03/beatuhri/beatuhri.htm.
Bedell, "Processing and Hydrolytic Degradation of Aromatic, Ortho-Substituted Polyanhydrides", Journal of Applied Polymer Science, 80, 32-38, (2001).
Brambley, et al., "Microlithography: an overview", Advanced Materials for Optics and Electronics, 4(2), 55-74, (Mar.-Apr. 1994).
Branch, "Microstamp patterns of biomolecules for high resolution neuronal networks", Medical & Biological Engineering & Computing, 36(1), 135-41, (Jan. 1998).
Brown, "A Polymeric Drug for Treatment of Inflammatory Bowel Disease", Journal of Medicinal Chemistry, 26(9), 1300-1307, (1983).
Brown, et al., "Transdermal delivery of drugs", Annual Review of Medicine, 39, 221-9, (1988).
Campo, "Polyanhydrides: the effects of ring substitution changes on polymer properties", Polymer Bulletin, 42, 61-68, (1999).
Carbone, et al., "Design and Synthesis of Fast-Degrading Poly(anhydride-esters)", Macromol. Rapid Commun., 30, 1021-1026 (2009).
Chafi, "Dosage Form with Salicylic Acid Attached to the Polyanhydride Polymer Dispersed in an Eudragit Matrix", International Journal of Pharmaceutics, 52, 203-211, (1989).
Chatterjee, et al., "Mechanism for the Increase in Solubility of Deoxyhemoglobin S due to Cross-Linking the Beta Chains Between Lysine-82 Beta1 and Lysine-82 Beta 2", Biochemistry, 21, 5901-5909, (1982).
Chen, "Effect of protein and cell behavior on pattern-grafted thermoresponsive polymer", Journal of Biomedical Materials Research, 42(1), 38-44, (Oct. 1998).
Conix, "Aromatic Polyanhydrides, a New Class of High Melting Fiber-Forming Polymers", Journal of Polymers Science, XXIX, 343-353, (1958).
Conix, "New High-Melting Fibre-Forming Polymers", Die Makromolekulare Chemie, XXIV, 76-78, (1957).
Conix, "Poly [1,3-bis (p carboxyphenoxy)—Propane anhydride]", Macromolecular Synthesis, 2, 95-99, (1996).
Cotlier, "Distribution of salicylate in lens and intraocular fluids and its effect on cataract formation", American Journal of Medicine, 74 (6A), 83-90 (1983).
Cotlier, "Senile Cataracts: Evidence for Acceleration by Diabetes and Deceleration by Salicytate", Canadian Journal of Ophthalmology, 16(3), 113-118 (1981).
Davaran, "Release of 5-amino Salicylic Acid from Acrylic Type Polymeric Prodrugs Designed for Colon-specific Drug Delivery", Journal of Controlled Release, 58(3), 279-287, (1999).
Davies, "The Analysis of the Surface Chemical Structure of Biomedical Aliphatic Polyanhydrides Using SPX and ToF-SIMS", Journal of Applied Polymer Science, 42, No. 6, New York, US, 1597-1605, (Mar. 20, 1991).
Delamarche, et al., "Patterned delivery of immunoglobulins to surfaces using microfluidic networks", Science, 276 (5313), 779-781, (May 2, 1997).
Dewez, et al., "Adhesion of mammalian cells to polymer surfaces: from physical chemistry of surfaces to selective adhesion on defined patterns", Biomaterials, 19(16), 1441-1445, (Aug. 1998).
Domb, "Polyanhydrides. I. Preparation of High Molecular Weight Polyanhydrides", Journal of Polymer Science: Part A: Polymer Chemistry, 25, 3373-3386, (1987).
Domb, "Synthesis and Characterization of Biodegradable Aromatic Anhydride Copolymers", Macromolecules, 25, 12-17, (1992).
Dontha, "Generation of biotin/avidin/enzyme nanostructures with maskless photolithography", Analytical Chemistry, 69(14), 2619-25, (Jul. 15, 1997).
Dugaiczyk, et al., "Nucleotide sequence and the encoded amino acids of human serum albumin mRNA", Proc. Natl Acad Sci, vol. 79, 71-75 (1982).
Dukovic, "Novel degradable poly(anhydride-esters) for controlled drug release", The Rutgers Scholar—An Electronic Bulletin of Undergraduate Research, 1, 1-10, (1999), http://www.scils.rutgers.edu/~weyang/ejournal/volume01/uhriduko/uhriduko.htm.

(56) References Cited

OTHER PUBLICATIONS

Erdman, et al., "Synthesis and Characterization of a Polymeric Prodrug", Proceedings of the American Chemical Society Division of Polymeric Materials: Science and Engineering, 78, Abstract Spring Meeting, Dallas, TX, pp. 194, (Apr. 1998).

Erdmann, et al., "Chapter 5, Polymeric Prodrugs: Novel Polymers with Bioactive Components in Tailored Polymeric Materials for Controlled Delivery Systems", ACS Symposium Series 709, Developed from a symposium sponsored by the Division of Polymer Chemistry at the 214th National Meeting of the American Chemical Society, Washington D.C., 83-91 (1998).

Erdmann, "Degradable poly(anhydride ester) implants: effects of localized salicylic acid release on bone", Biomaterials, 21(24), 2507-2512, (2000).

Erdmann, "Polymer Prodrugs with Pharmaceutically Active Degradation Products", Polymer Preprints, 38(2), 570-571, Proceedings of the 1997 American Chemical Society Las Vegas Meeting, Las Vegas, NV (Sep. 7-12, 1997).

Erdmann, "Polymeric Prodrugs: Novel Polymers for Delivery of Salicylic Acid", Annals of Biomedical Engineering, 26 (Suppl. 1), Abstract No. PB26, Annual Fall Meeting, S-124, (1998).

Erdmann, "Polymeric Salicylic Acid: In Vitro and In Vivo Degradation", Polymer Preprints, 39(2), 224-225, (1998).

Erdmann, et al., "Synthesis and degradation characteristics of salicylic acid-derived poly(anhydride-esters)", Biomaterials 21(19), 1941-1946 (2000).

Faig, et al., "PolyKojic Acid: From Meat to Makeup", National American Chemical Society, Abstract, 1 page, Boston, MA (Jun. 22, 2015).

Giammona, "Polymeric Prodrugs alpha beta poly-hyroxyethyl-dl-aspartamide as macromolecular carrier for some non-steroidal anti-inflammatory agents", Abstracts from Database BIOSIS Online, Biosciences Information Service, Philadelphia, PA, Original Publication from the International Journal of Pharmaceutics (Amsterdam), 1 page (1989).

Giammona, "Polymeric Prodrugs Alpha Beta Poly-N-hydroxyethyl-DL-aspartamide as a Macromolecular Carrier for Some Non-Steroidal Anti-inflammatory Agents", International Journal of Pharmaceutics, 57, 55-62, (1989).

Gouin, et al., "New Polyanhydrides Made from a Bile Acid Dimer and Sebacic Acid: Synthesis, Characterization and Degradation", Macromolecules, 33, 5379-5383, (2000).

Herbert, "Micropatterning gradients and controlling surface densities of photoactivatable biomolecules on self-assembled monolayers of oligo(ethylene glycol) alkanethiolates", Chemistry & Biology, 4(10), 731-7, (Oct. 1997).

Ibim, "Controlled Release Based on Poly(anhydride-co-imides)", Proc. Intern. Symp. Control. Rel. Bioact. Mater., 22, 2 pgs, (1995).

Ibim, "Poly(anhydride-co-imides): In Vivo Biocompatibility in a rat model", Biomaterials, 19(10), 941-951, (1998).

Faig, et al., "PolyKojic Acid: From Meat to Makeup", Presentation at National American Chemical Society Meeting, Boston MA, 15 pages, Aug. 2015.

* cited by examiner

KOJIC ACID POLYMERS

CROSS-REFERENCE TO RELATED APPLICATION(S)

This application claims priority from U.S. Provisional Application No. 62/146,027, filed Apr. 10, 2015, which application is herein incorporated by reference.

BACKGROUND OF THE INVENTION

Kojic acid (5-Hydroxy-2-(hydroxymethyl)-4-pyrone), a natural tyrosinase inhibitor possessing antimicrobial and antioxidant activity, is commonly utilized in personal care products as a skin lightener and in the food industry as a natural preservative. While effective, kojic acid's inclination to undergo thermal and photodegradation impairs its efficacy and makes it less desirable as an active agent commercially.

Although kojic acid has recently been grafted onto chitosan polymers, it has not been incorporated into a polymer backbone. Additionally, while kojic acid is utilized as a food additive, complex systems (such as kojic acid polymer films) have not been explored.

There is currently a need for a form of kojic acid or a formulation of kojic acid that has improved stability properties. Such a formulation or form would make kojic acid a more viable active agent for an expanded list of applications. Accordingly, a controlled release system for kojic acid having improved stability is desirable.

SUMMARY OF THE INVENTION

A controlled release system for kojic acid having improved stability has been identified. To minimize degradation, kojic acid was incorporated into a hydrolytically degradable polymer (e.g., a poly(carbonate-ester)). By synthesizing polymer precursors containing kojic acid-linker-kojic acid chemical structures, versatile monomers were developed that can be used to modulate polymer properties. Additionally the synthetic method lends itself to the development of other polymer systems.

Polymer physicochemical properties were characterized by nuclear magnetic resonance and Fourier transform infrared spectroscopies, whereas gel permeation chromatography was employed to assess polymer weight-averaged molecular weight and polydispersity index data. Thermal properties were evaluated and polymer stability examined. Polymer hydrolytic degradation was investigated under physiological conditions to determine kojic acid-based poly(carbonate-ester's) release profile and degradation media bioactivity assessed against identical concentrations of free kojic acid. The polymers comprising kojic acid are useful, for example, in the manufacture of films capable of releasing kojic acid in a sustained manner for personal care and active packaging applications.

Accordingly the invention provides a polymer having a backbone wherein the backbone comprises one or more groups that will yield kojic acid upon degradation of the polymer.

The invention also provides a pharmaceutical composition comprising a polymer of the invention and a pharmaceutically acceptable carrier.

The invention also provides a cosmetic formulation comprising a polymer of the invention and an acceptable carrier.

The invention also provides film comprising a polymer of the invention.

The invention also provides a packing material (e.g. an active packaging material) comprising a polymer of the invention.

The invention also provides a method comprising delivering kojic acid to a surface (e.g. a counter top, a desk top, or skin), comprising contacting the surface with a polymer of the invention.

The invention also provides a method for the treating a disease, disorder or condition in a mammal comprising administering an effective amount of a polymer as described herein to the mammal.

The invention provides a polymer of the invention for use in medical therapy, as well as the use of a polymer of the invention for the manufacture of a medicament useful for the treatment of a disease, disorder or condition in a mammal, such as a human.

The invention also provides processes and intermediates disclosed herein that are useful for preparing a polymer of the invention.

BRIEF DESCRIPTION OF THE FIGURES

FIG. 4A shows a schematic of the in vitro studies, which were performed using phosphate buffered saline (PBS, pH 7.4) at 37° C., mimicking physiological conditions. FIG. 4B shows the proposed hydrolytic degradation pathway of polymer 5. Hydrolysis first occurs at the carbonate site to release monomer 4, followed ester hydrolysis to release kojic acid. UV-Vis analyses were performed at $\lambda=270$ nm. FIG. 4C shows the cumulative percentage of kojic acid release over 30 days for polymer (5c) and (5d). As shown, the release rate increased with decreasing linker molecule length.

DETAILED DESCRIPTION

Figure 1:
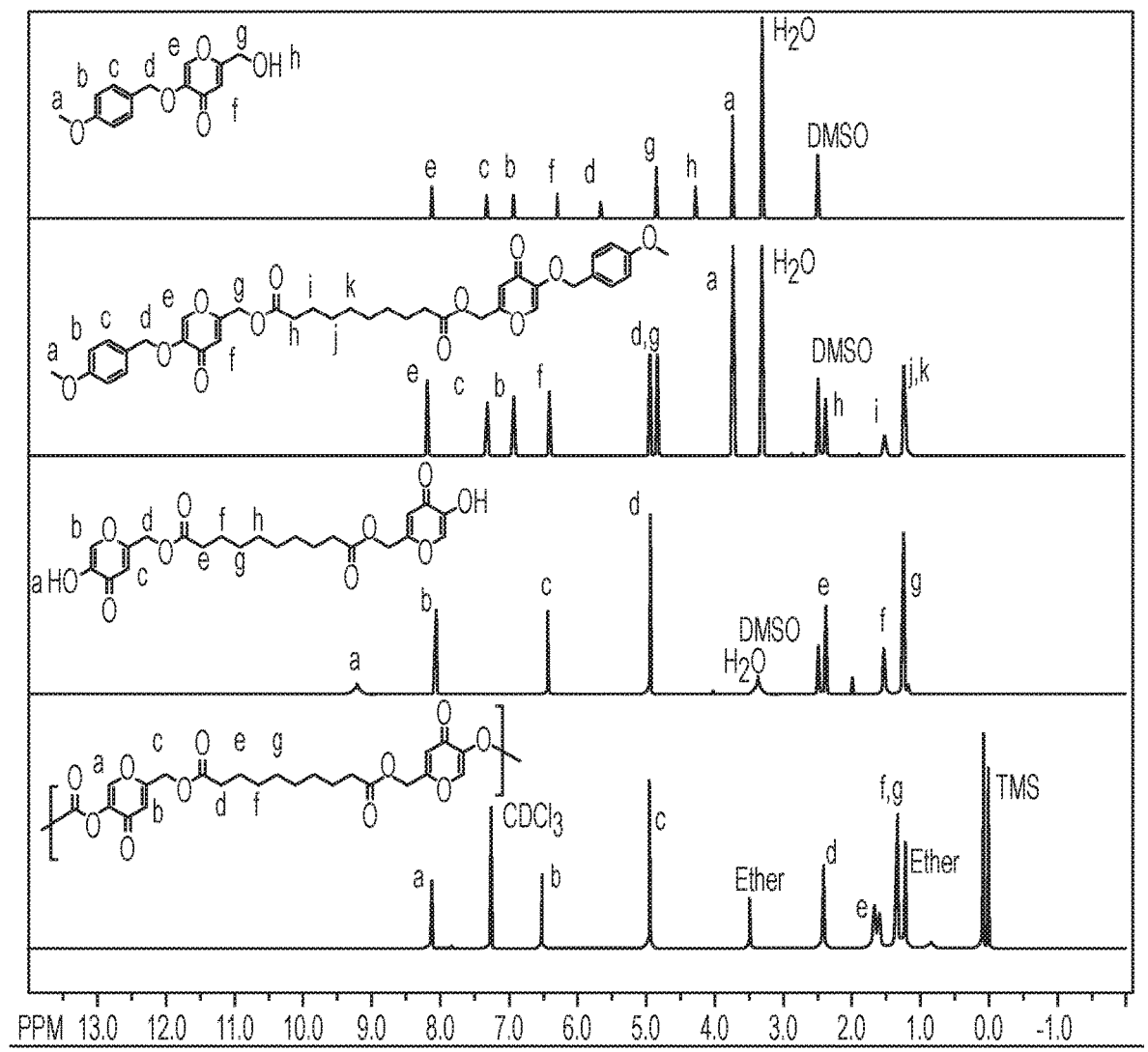
FIG. 1 shows the NMR spectra for compound 101 and for compounds 102, 103, and 4 wherein R was derived from sebacic acid.

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_6$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenyl-alanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide; or as an α-methylbenzyl amide). Other suitable amino and carboxy protecting groups are known to those skilled in the art (See for example, Greene, T. W.; Wutz, P. G. M. "Protecting Groups In Organic Synthesis" second edition, 1991, New York, John Wiley & sons, Inc., and references cited therein).

The term "peptide" describes a sequence of 2 to 35 amino acids (e.g. as defined hereinabove) or peptidyl residues. The sequence may be linear or cyclic. For example, a cyclic peptide can be prepared or may result from the formation of disulfide bridges between two cysteine residues in a sequence. Preferably a peptide comprises 3 to 20, or 5 to 15 amino acids. Peptide derivatives can be prepared as disclosed in U.S. Pat. Nos. 4,612,302; 4,853,371; and 4,684,620, or as described in the Examples hereinbelow. Peptide sequences specifically recited herein are written with the amino terminus on the left and the carboxy terminus on the right.

Polymers of the Invention

The polymers of the invention are useful in a variety of applications where delivery of kojic acid is desired. Examples of such applications include, but are not limited to, cosmetic applications, personal care applications, and active packaging applications.

The polymers of the invention may be prepared in accordance with methods commonly employed in the field of synthetic polymers to produce a variety of useful products with valuable physical and chemical properties. The polymers can be readily processed into pastes or solvent cast to yield films, coatings, microspheres and fibers with different geometric shapes for design of various medical implants, and may also be processed by compression molding and extrusion.

Polymers of the present invention can also be incorporated into products such as skin moisturizers, cleansers, pads, plasters, lotions, creams, gels, ointments, solutions, shampoos, tanning products and lipsticks.

The invention provides homopolymers and mixed polymers that comprise kojic acid. The mechanical and hydrolytic properties of the polymers can be controlled, for example, by modifying the group (R) and/or the group ($R^3$) in the polymer backbone.

The polymers of the present invention typically have average molecular weights ranging between about 1500 daltons up to about 100,000 daltons, calculated by Gel Permeation Chromatography (GPC) relative to narrow molecular weight polystyrene standards. Certain specific polymers have average molecular weights of about 1500 daltons, up to about 50,000 daltons calculated by Gel Permeation Chromatography (GPC) relative to narrow molecular weight polystyrene standards. Other specific polymers have average molecular weights of about 1500 daltons, up to about 35,000 daltons.

Accordingly, certain embodiments of the invention provide a polymer having a backbone wherein the backbone comprises one or more groups that will yield kojic acid upon degradation of the polymer.

In certain embodiments, the polymer is a polyester, a polyamide, a polyanhydride, a polycarbonate, or a polycarbamate, or a copolymer thereof.

In certain embodiments, the polymer is a copolymer that comprises one or more repeating units comprising a polyester, a polyamide, a polyanhydride, a polycarbonate, or a polycarbamate.

In certain embodiments, the polymer comprises one or more polyester or polycarbonate units that comprise one or more groups that will yield kojic acid upon degradation of the unit.

Certain embodiments of the invention provide a polymer that comprises one or more units of formula (I):

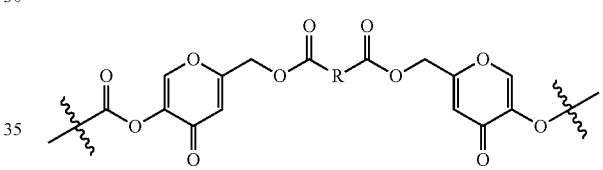

wherein:

R is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—$NR_a$—), wherein the chain is optionally substituted on carbon with one or more (e.g. 1, 2, 3, or 4) substituents selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy, and wherein $R_a$— is H or $C_1$-$C_6$ alkyl.

Certain embodiments of the invention provide a polymer of formula 5:

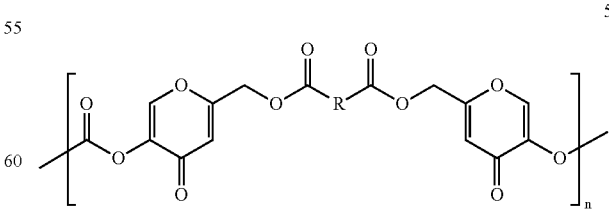

wherein:

R is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—NR$_a$—), wherein the chain is optionally substituted on carbon with one or more (e.g. 1, 2, 3, or 4) substituents selected from the group consisting of (C$_1$-C$_6$)alkoxy, (C$_3$-C$_6$)cycloalkyl, (C$_1$-C$_6$)alkanoyl, (C$_1$-C$_6$)alkanoyloxy, (C$_1$-C$_6$)alkoxycarbonyl, (C$_1$-C$_6$)alkylthio, azido, cyano, nitro, halo, hydroxy, oxo, carboxy, aryl, aryloxy, heteroaryl, and heteroaryloxy; wherein R$_a$ is H or C$_1$-C$_6$ alkyl; and n is an integer from 2 to 500 inclusive.

In certain embodiments, n is an integer from 5 to 300, inclusive. In certain embodiments, n is an integer from 10 to 300, inclusive. In certain embodiments, n is an integer from 15 to 300, inclusive. In certain embodiments, n is an integer from 20 to 300, inclusive. In certain embodiments, n is an integer from 20 to 250, inclusive. In certain embodiments, n is an integer from 50 to 250, inclusive.

In certain embodiments, R may be any value as described herein.

Certain embodiments of the invention also provide a polymer that comprises one or more units of formula (II):

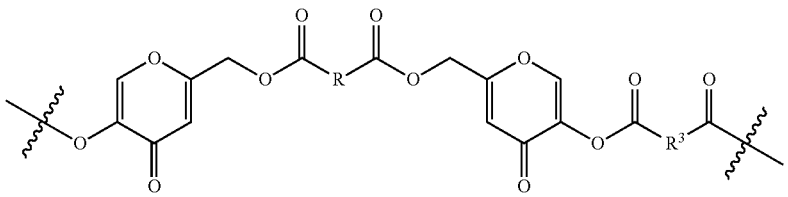

wherein:

R and R$^3$ are each independently a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—NR$_a$—), wherein the chain is optionally substituted on carbon with one or more (e.g. 1, 2, 3, or 4) substituents selected from the group consisting of (C$_1$-C$_6$)alkoxy, (C$_3$-C$_6$)cycloalkyl, (C$_1$-C$_6$)alkanoyl, (C$_1$-C$_6$)alkanoyloxy, (C$_1$-C$_6$)alkoxycarbonyl, (C$_1$-C$_6$)alkylthio, azido, cyano, nitro, halo, hydroxy, oxo, carboxy, aryl, aryloxy, heteroaryl, and heteroaryloxy, and wherein R$_a$ is H or C$_1$-C$_6$ alkyl.

Certain embodiments of the invention provide a polymer of formula 6:

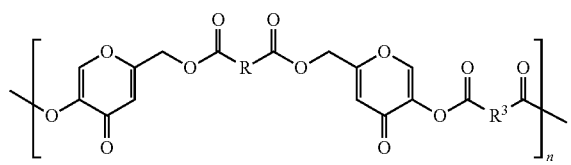

wherein:

R and R$^3$ are each independently a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—NR$_a$—), wherein the chain is optionally substituted on carbon with one or more (e.g. 1, 2, 3, or 4) substituents selected from the group consisting of (C$_1$-C$_6$)alkoxy, (C$_3$-C$_6$)cycloalkyl, (C$_1$-C$_6$)alkanoyl, (C$_1$-C$_6$)al-kanoyloxy, (C$_1$-C$_6$)alkoxycarbonyl, (C$_1$-C$_6$)alkylthio, azido, cyano, nitro, halo, hydroxy, oxo, carboxy, aryl, aryloxy, heteroaryl, and heteroaryloxy; wherein R$_a$ is H or C$_1$-C$_6$ alkyl; and n is an integer from 2 to 500 inclusive.

In certain embodiments, n is an integer from 5 to 300, inclusive. In certain embodiments, n is an integer from 10 to 300, inclusive. In certain embodiments, n is an integer from 15 to 300, inclusive. In certain embodiments, n is an integer from 20 to 300, inclusive. In certain embodiments, n is an integer from 20 to 250, inclusive. In certain embodiments, n is an integer from 50 to 250, inclusive.

In certain embodiments, R and R$^3$ are any value as described herein.

Compositions, Formulations, Materials and Films

Certain embodiments of the invention provide a pharmaceutical composition comprising a polymer as described herein and a pharmaceutically acceptable carrier.

Certain embodiments of the invention provide a cosmetic formulation comprising a polymer as described herein and an acceptable carrier (e.g., a dermatologically acceptable carrier).

Certain embodiments of the invention provide a film comprising a polymer as described herein.

Certain embodiments of the invention provide packing material (e.g., an active packing material) comprising a polymer as described herein.

Methods of Use

Certain embodiments of the invention provide a method comprising delivering kojic acid to a surface comprising contacting the surface with a polymer as described herein.

In certain embodiments, the surface is, e.g., a counter top, a desk top or skin.

Certain embodiments of the invention provide a polymer of the invention for use in medical therapy.

Certain embodiments of the invention provide a method for treating a disease, disorder or condition in a mammal (e.g., a human) comprising administering an effective amount of a polymer of the invention to the mammal. In certain embodiments the polymer is administered topically.

Certain embodiments of the invention provide a polymer of the invention for the prophylactic or therapeutic treatment of a disease, disorder or condition.

Certain embodiments of the invention provide the use of a polymer of the invention for the manufacture of a medicament useful for the treatment of a disease, disorder or condition in a mammal, such as a human.

In certain embodiments, the disease, disorder or condition is a hyperpigmentation disorder. As described herein, a hyperpigmentation disorder includes, but is not limited to, post-inflammatory hyperpigmentation, melasma, and lentigines.

Synthetic Methods

Certain embodiments of the invention provide a method for preparing a polymer of formula 5:

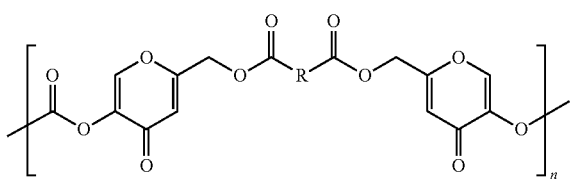

wherein:
R is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—$NR_a$—), wherein the chain is optionally substituted on carbon with one or more (e.g. 1, 2, 3, or 4) substituents selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy; and wherein $R_a$ is H or $C_1$-$C_6$ alkyl; and n is an integer from 2 to 500 inclusive comprising polymerizing a corresponding diol of formula 4:

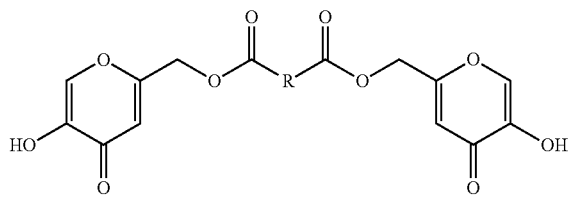

to provide the polymer of formula 5.

In certain embodiments, the diol of formula 4 is polymerized in solution. In certain embodiments, the solution comprises dichloromethane.

In certain embodiments, the diol of formula 4 is polymerized by treatment with triphosgene in the presence of a base. In certain embodiments, the base is an amine base. In certain embodiments, the amine base is triethylamine.

Certain embodiments of the invention provide a method for preparing a polymer of formula 6:

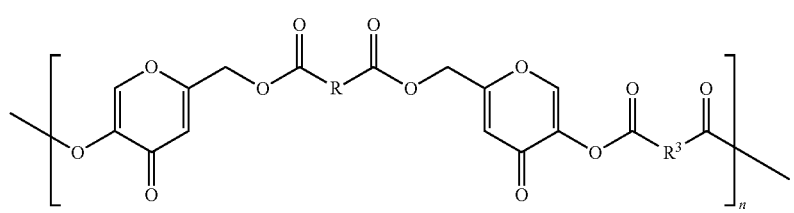

wherein:
R and $R^3$ are each independently a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—$NR_a$—), wherein the chain is optionally substituted on carbon with one or more (e.g. 1, 2, 3, or 4) substituents selected from the group consisting of ($C_1$-$C_6$) alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy; wherein $R_a$ is H or $C_1$-$C_6$ alkyl; and n is an integer from 2 to 500 inclusive, comprising reacting a corresponding diol of formula 4:

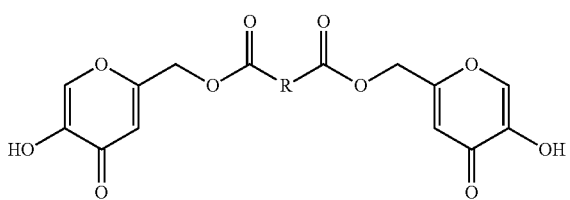

with a corresponding diacid chloride of formula:

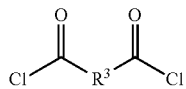

to provide the polymer of formula 6.

In certain embodiments, the reaction is carried out in solution. In certain embodiments, the polymerization is carried out in the presence of a base. In certain embodiments, the base is an amine base, such as triethylamine.

Compounds of the Invention

Certain embodiments of the invention provide a compound of formula 1:

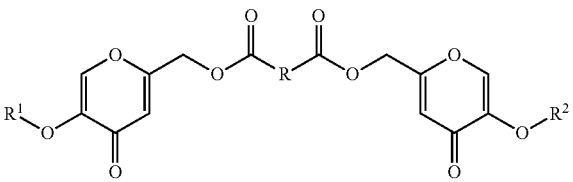

wherein:
R is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—$NR_a$—), wherein the chain is optionally substituted on carbon with one or more (e.g. 1, 2, 3, or 4) substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy; wherein $R_a$ is H or $C_1$-$C_6$ alkyl;

$R^1$ is H or a hydroxy protecting group; and
$R^2$ is H or a hydroxy protecting group.

In certain embodiments, R may be any value as described herein.

In certain embodiments, $R^1$ is 4-methoxybenzyl.
In certain embodiments, $R^1$ is H.
In certain embodiments, $R^2$ is 4-methoxybenzyl.
In certain embodiments, $R^2$ is H.

Linking Group "R"

The nature of the linking group "R" in a polymer of the invention is not critical provided the polymer of the invention possesses acceptable mechanical properties and release kinetics for the selected application. The linking group R is typically a divalent organic radical having a molecular weight of from about 25 daltons to about 400 daltons. More specifically, R has a molecular weight of from about 40 daltons to about 200 daltons.

The linking group R typically has a length of from about 5 angstroms to about 100 angstroms using standard bond lengths and angles. More specifically, the linking group R has a length of from about 10 angstroms to about 50 angstroms.

The linking group R may be biologically inactive, or may itself possess biological activity. The linking group R can also comprise other functional groups (including hydroxy groups, mercapto groups, amine groups, carboxylic acids, as well as others) that can be used to modify the properties of the polymer (e.g. for branching, for cross linking, for appending other molecules (e.g. another biologically active compound) to the polymer, for changing the solubility of the polymer, or for effecting the biodistribution of the polymer).

Linking Group "$R^3$"

The nature of the linking group "$R^3$" in a polymer of the invention is not critical provided the polymer of the invention possesses acceptable mechanical properties and release kinetics for the selected application. The linking group $R^3$ is typically a divalent organic radical having a molecular weight of from about 25 daltons to about 400 daltons. More specifically, $R^3$ has a molecular weight of from about 40 daltons to about 200 daltons.

The linking group $R^3$ typically has a length of from about 5 angstroms to about 100 angstroms using standard bond lengths and angles. More specifically, the linking group $R^3$ has a length of from about 10 angstroms to about 50 angstroms.

The linking group $R^3$ may be biologically inactive, or may itself possess biological activity. The linking group $R^3$ can also comprise other functional groups (including hydroxy groups, mercapto groups, amine groups, carboxylic acids, as well as others) that can be used to modify the properties of the polymer (e.g. for branching, for cross linking, for appending other molecules (e.g. another biologically active compound) to the polymer, for changing the solubility of the polymer, or for effecting the biodistribution of the polymer).

Specific Values

Specific values listed herein for radicals, substituents, groups, and ranges, are for illustration only; they do not exclude other defined values or other values within defined ranges for the radicals and substituents.

Specifically, $(C_1-C_6)$alkyl can be methyl, ethyl, propyl, isopropyl, butyl, isobutyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for R is a divalent, branched or unbranched, saturated or unsaturated, hydrocarbon chain, having from 1 to 20 carbon atoms, wherein the chain is optionally substituted on carbon with one or more (e.g. 1, 2, 3, or 4) substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy.

Another specific value for R is an amino acid.

Another specific value for R is a peptide

Another specific value for R is a divalent, branched or unbranched, saturated or unsaturated, hydrocarbon chain, having from 1 to 20 carbon atoms, wherein one or more (e.g. 1, 2, 3, or 4) of the carbon atoms is optionally replaced by (—O—) or (—NR$_a$—), and wherein R$_a$ is H or $C_1$-$C_6$ alkyl.

Another specific value for R is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR$_a$—), wherein the chain is optionally substituted on carbon with one or more (e.g. 1, 2, 3, or 4) substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy, and wherein R$_a$ is H or $C_1$-$C_6$ alkyl.

Another specific value for R is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR$_a$), and wherein R$_a$ is H or $C_1$-$C_6$ alkyl.

Another specific value for R is a divalent, branched or unbranched, saturated or unsaturated, hydrocarbon chain, having from 3 to 15 carbon atoms.

Another specific value for R is a divalent, branched or unbranched, hydrocarbon chain, having from 3 to 15 carbon atoms.

Another specific value for R is a divalent, branched or unbranched, hydrocarbon chain, having from 6 to 10 carbon atoms.

Another specific value for R is a divalent hydrocarbon chain having 7, 8, or 9 carbon atoms.

Another specific value for R is a divalent hydrocarbon chain having 8 carbon atoms.

Another specific value for R is a divalent hydrocarbon chain having 2, 3, 4, 5, 6, 7, 8, or 9 carbon atoms.

Another specific value for R is a divalent hydrocarbon chain having 2, 4, or 8 carbon atoms.

Another specific value for R is a divalent hydrocarbon chain having 2, 4, 7 or 8 carbon atoms. Another specific value for R is —$(CH_2OCH_2)_3$—.

A specific value for $R^3$ is a divalent, branched or unbranched, saturated or unsaturated, hydrocarbon chain, having from 1 to 20 carbon atoms, wherein the chain is optionally substituted on carbon with one or more (e.g. 1, 2, 3, or 4) substituents selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy.

Another specific value for $R^3$ is an amino acid.

Another specific value for $R^3$ is a peptide

Another specific value for $R^3$ is a divalent, branched or unbranched, saturated or unsaturated, hydrocarbon chain, having from 1 to 20 carbon atoms, wherein one or more (e.g. 1, 2, 3, or 4) of the carbon atoms is optionally replaced by (—O—) or (—$NR_a$—), and wherein $R_a$ is H or $C_1$-$C_6$ alkyl.

Another specific value for $R^3$ is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—$NR_a$—), wherein the chain is optionally substituted on carbon with one or more (e.g. 1, 2, 3, or 4) substituents selected from the group consisting of ($C_1$-$C_6$) alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy, and wherein $R_a$ is H or $C_1$-$C_6$ alkyl.

Another specific value for $R^3$ is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—$NR_a$—), and wherein $R_a$ is H or $C_1$-$C_6$ alkyl.

Another specific value for $R^3$ is a divalent, branched or unbranched, saturated or unsaturated, hydrocarbon chain, having from 3 to 15 carbon atoms.

Another specific value for $R^3$ is a divalent, branched or unbranched, hydrocarbon chain, having from 3 to 15 carbon atoms.

Another specific value for $R^3$ is a divalent, branched or unbranched, hydrocarbon chain, having from 6 to 10 carbon atoms.

Another specific value for $R^3$ is a divalent hydrocarbon chain having 7, 8, or 9 carbon atoms.

Another specific value for $R^3$ is a divalent hydrocarbon chain having 8 carbon atoms.

Another specific value for $R^3$ is a divalent hydrocarbon chain having 2, 3, 4, 5, 6, 7, 8, or 9 carbon atoms.

Another specific value for $R^3$ is a divalent hydrocarbon chain having 2, 4, or 8 carbon atoms.

Another specific value for $R^3$ is a divalent hydrocarbon chain having 2, 4, 7 or 8 carbon atoms.

Another specific value for $R^3$ is —$(CH_2OCH_2)_3$—.

Another specific value for $R^3$ is a divalent hydrocarbon chain having 4 carbon atoms.

In another specific embodiment, R is a divalent hydrocarbon chain having 2, 4, 7 or 8 carbon atoms or R is —$(CH_2OCH_2)_3$— and $R^3$ is a divalent hydrocarbon chain having 4 carbon atoms.

Administration

The polymers of the invention can be formulated as pharmaceutical compositions and administered to a mammalian host, such as a human patient in a variety of forms adapted to the chosen route of administration, i.e., orally, rectally, or parenterally, by intravenous, intramuscular, intraperitoneal, intraspinal, intracranial, topical, ocular or subcutaneous routes. For some routes of administration, the polymer can conveniently be formulated as micronized particles.

Thus, the polymers of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations preferably contain at least 0.1% of polymer by weight. The percentage of the compositions and preparations may, of course, be varied and may conveniently be between about 2 to about 80% of the weight and preferably 2 to about 60% of a given unit dosage form. The amount of polymer in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The polymer may also be administered intravenously, intraspinal, intracranial, or intraperitoneally by infusion or injection. Solutions of the polymer can be prepared a suitable solvent such as an alcohol, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile solutions or dispersions or sterile powders comprising the polymer containing the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the polymer in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present polymers can be applied in pure form. However, it will generally be desirable to administer them as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include, alcohols or glycols or alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the polymers of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Characterization

Polymeric drug delivery systems of the present invention can be characterized by proton nuclear magnetic resonance (NMR) spectroscopy, infrared (IR) spectroscopy, gel permeation chromatography (GPC), high performance liquid chromatography (HPLC), differential scanning calorimetry (DSC), and thermal gravimetric analysis (TGA). For infrared spectroscopy, samples are prepared by solvent casting on NaCl plates. $^1$H and $^{13}$C NMR spectroscopy is obtained in solutions of $CDCl_3$ or $DMSO-d_6$ with solvent as the internal reference.

GPC can be performed to determine molecular weight and polydispersity. In this method, samples are dissolved in dichloromethane and eluted through a mixed bed column (Jordi divinylbenzyl, mixed bed, 7.8×300 mm) at a flow rate of 1.0 mL/minute. Typically the samples (about 10 mg/mL) are dissolved into dichloromethane and filtered using 0.5 µm PTFE syringe filters prior to column injection. Molecular weights are determined relative to narrow molecular weight polystyrene standards (Polysciences, Inc.).

Thermal analysis can also be performed using a system such as the Perkin-Elmer system consisting of a TGA 7 thermal gravimetric analyzer equipped with PE AD-4 autobalance and Pyris 1 DSC analyzer. In this system, Pyris software is used to carry out data analysis on a DEC Venturis 5100 computer. For DSC, an average sample weight of 5-10 mg is heated at 10° C./minute at a 30 psi flow of $N_2$. For TGA, an average sample weight of 10 mg is heated at 20° C./minute under a 8 psi flow of $N_2$. Sessile drop contact angle measurements are obtained with an NRL Goniometer (Rame-hart) using distilled water. Solutions of polymer in methylene chloride (10% wt/volume) are spun-coated onto glass slips, at 5,000 rpm for 30 seconds.

Degradation and drug release profiles of the polymer drug delivery systems of the present invention can also be determined routinely. For these experiments, the polymers are processed into either films, pellets, microspheres, nanospheres or fibers (depending on their properties). After processing, the materials are be characterized to determine if any physicochemical changes have occurred during processing. Uniform processed, weighed, and characterized samples are then degraded in acidic, neutral, and basic phosphate buffer (conditions chosen to simulate physiological range) in triplicate. Periodically the buffer is removed and replaced with fresh media to simulate sink conditions. The spent buffer is analyzed by HPLC to determine the cumulative release of the drug. At defined time periods, samples are removed from the buffer and superficially dried (blotted). They are then weighed to determine the water uptake. At this point, the contact angle (hydrated) is also measured to determine changes in hydrophobicity during degradation. The samples are then thoroughly dried under vacuum and weighed to determine their mass loss. Contact angles (dry) are measured again to determine the hydrophobicity of the dry material, and how it compares to that of the hydrated material. By plotting cumulative release of the degradation products over time, the degradation kinetics can be defined. Wet and dry polymer weights over time indicate if the material is bulk or surface eroding. If there is an increase in water uptake, it can be determined that the polymer is bulk eroding, whereas if there is little or no water uptake the material is considered surface-eroding. By plotting the changes in dry weight versus time, the mass lost by the polymer as it erodes can be determined. This information will give additional insight into how the material is degrading. Changes in molecular weight over time are also examined to bolster the degradation results.

Polymers of the present invention can be isolated by known methods commonly employed in the field of synthetic polymers. Polymeric drug delivery systems of the invention can be readily processed into pastes or solvent cast to yield films, coatings, microspheres and fibers with different geometric shapes for design of various medical implants, and may also be processed by compression molding and extrusion. Medical implant applications include the use of polymers to form shaped articles such as vascular grafts and stents, bone plates, sutures, implantable sensors, implantable drug delivery devices, stents for tissue regeneration.

The invention will now be illustrated by the following non-limiting Examples.

EXAMPLES

Example 1. Synthesis of Representative Polymers of the Invention

Representative polymers of the invention were prepared as illustrated in Scheme 1 below.

Scheme 1. Synthesis of compounds and polymers of the invention. Other compounds and polymers of the invention, wherein R and R³ are defined as described herein may be synthesized using similar methods.

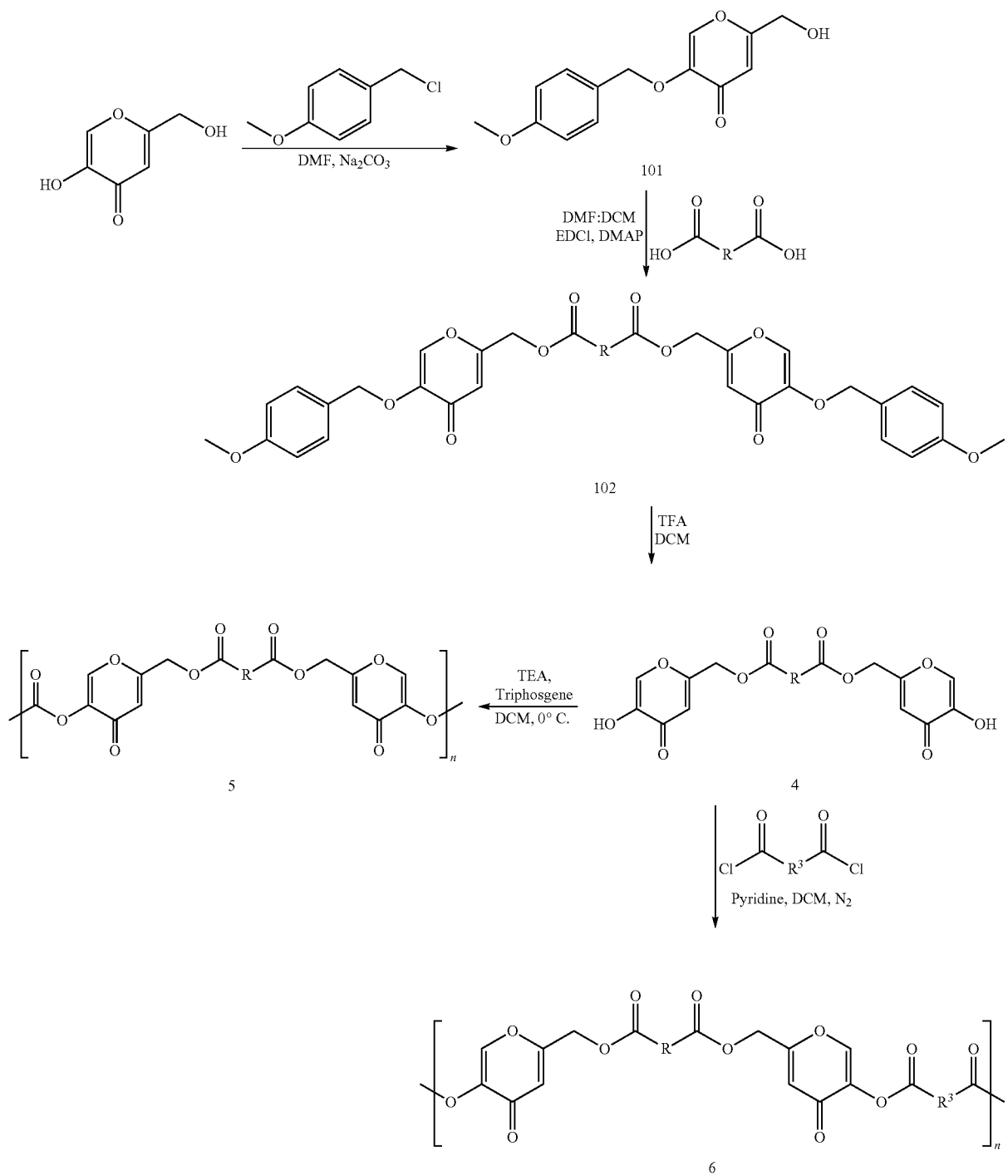

-continued

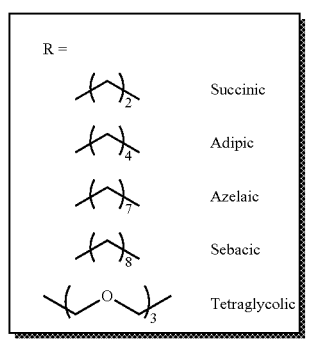
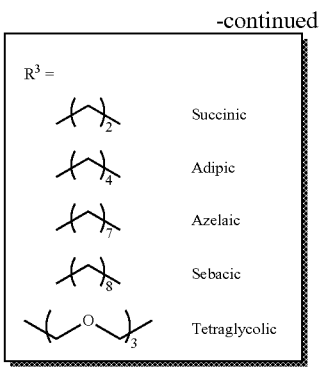

Figure 2:
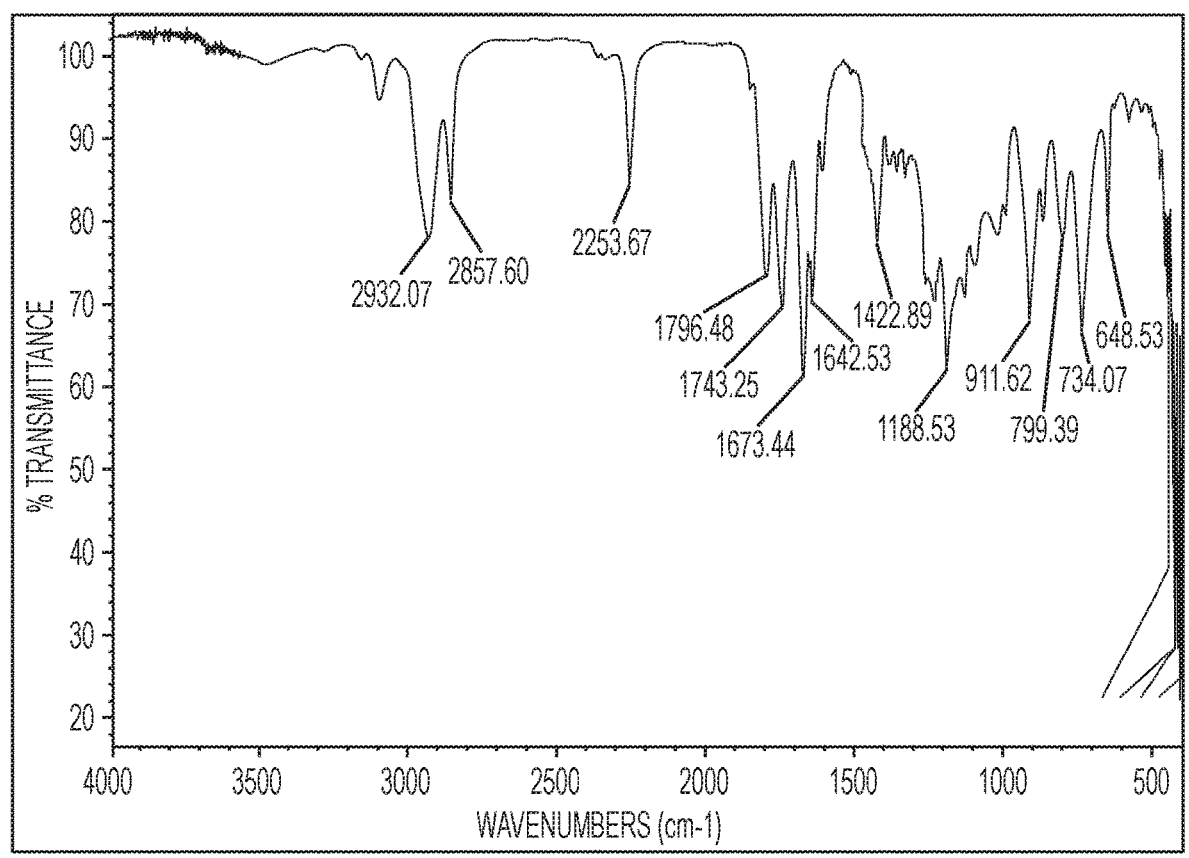
FIG. 2 shows the IR spectrum for compound 4, wherein R was derived from sebacic acid.
Figure 3:
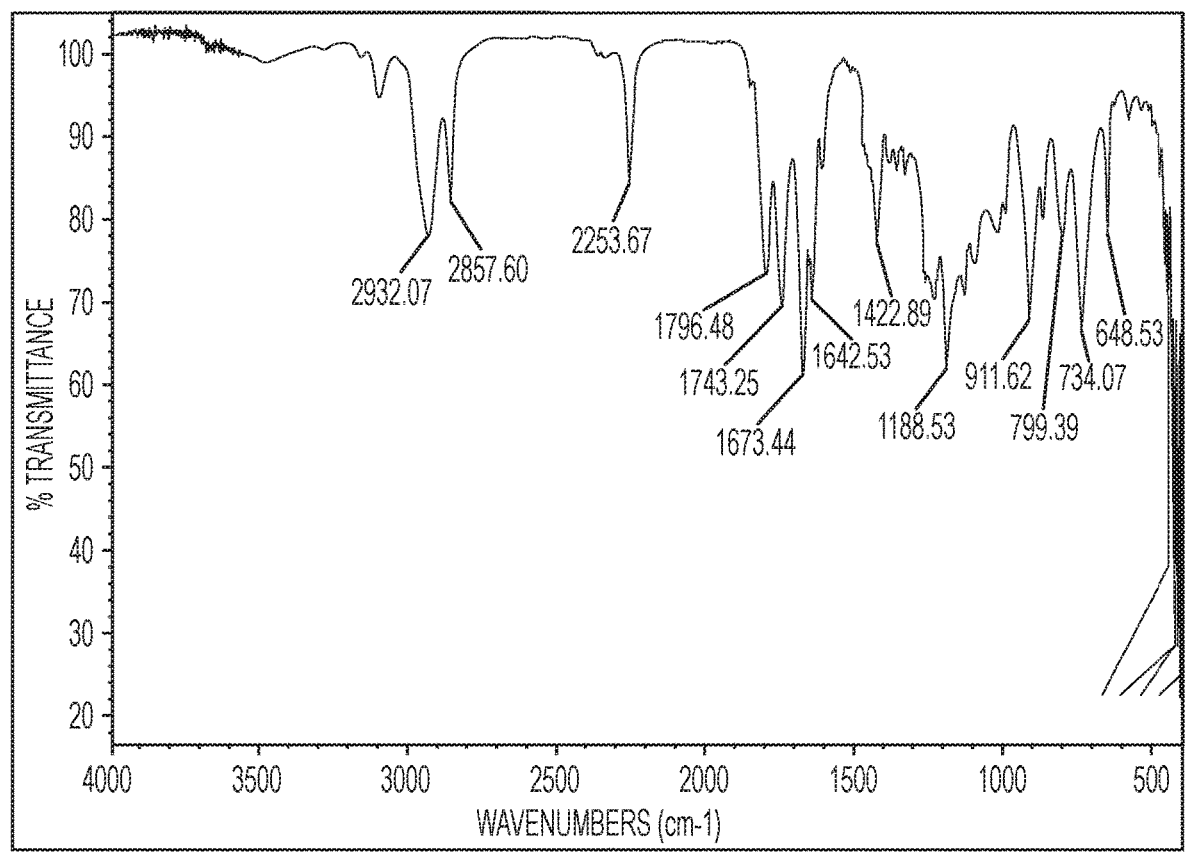
FIG. 3 shows an IR spectrum for polymer 5, wherein R was derived from sebacic acid.

Kojic acid (KA) was protected with paramethoxybenzyl chloride (PMB-Cl) and subsequently conjugated to a dicarboxylic acid (succinic, adipic, azelaic, sebacic, and tetraglycolic) via carbodiimide coupling. The resulting diester was selectively deprotected (e.g. using TFA) and the resulting dienol was polymerized by solution polymerization to produce the corresponding poly(carbonate-ester). NMR spectra for compound 101 and for compounds 102, 4, and 5 wherein R was derived from sebacic acid are shown in FIG. 1. An IR spectrum for compound 4, wherein R was derived from sebacic acid, is shown in FIG. 2; an IR spectrum for polymer 5, wherein R was derived from sebacic acid, is shown in FIG. 3; disappearance of the phenol peak at 3262 and the appearance of the carbonate peak at 1796 shows formation of the carbonate ester.

The resulting KA (sebacic acid) polymer was characterized. Data is shown in the following Table.

| Polymer | Tg | Decomposition Temperature | Molecular Weight (kDa) | PDI |
|---|---|---|---|---|
| KA (Sebacic) | 15° C. | 208° C. | 18.0 | 1.8 |

Polymer 6 may also be prepared as shown in Scheme 1 and characterized in manner similar to polymer 5.

Example 2. Synthesis and Characterization of Polymers and Dienols Comprising Kojic Acid Tyrosinase, a copper-containing enzyme and key regulator of melanin biosynthesis, catalyzes distinct reactions in the melanogenic cascade (Slominski, et al., *Physiol Rev* 2004, 84, 1155-1228). More specifically, tyrosinase facilitates the hydroxylation of L-tyrosine to L-dihydroxyphenylalanine (L-DOPA) and the subsequent L-DOPA oxidation (Slominski, et al., *Physiol Rev* 2004, 84, 1155-1228), the former which is rate-determining (Chang, *Materials* 2012, 5, (12), 1661-1685), in concerted or concurrent steps in the initial melanin biosynthesis (Solomon, et al., *Chemical Reviews* 1996, 96, 2563-2605). The two copper ions present in tyrosinase's active site are important in the catalysis of the aforementioned reaction (Solomon, et al., *Chemical Reviews* 1996, 96, 2563-2605); thus considerable research has focused on tyrosinase inhibition (Chang, *International journal of molecular sciences* 2009, 10, (6), 2440-75).

Kojic acid, a natural tyrosinase inhibitor possessing antimicrobial and antioxidant activity, is commonly utilized in personal care products as a skin lightener and in the food industry as a natural preservative. While effective, kojic acid's inclination to undergo thermal and photodegradation impairs its efficacy, necessitating the development of novel delivery systems. Thus, to overcome these deficiencies and minimize degradation, kojic acid was incorporated into hydrolytically degradable poly(carbonate-esters) and polyesters with naturally occurring diacids through solution polymerization methods. By synthesizing polymer precursors containing kojic acid-linker-kojic acid chemical structures, versatile monomers were developed capable modulating polymer properties. Polymer physicochemical properties were characterized by nuclear magnetic resonance and Fourier transform infrared spectroscopies, whereas gel permeation chromatography was employed to assess polymer weight-averaged molecular weight and polydispersity index data. Thermal properties were evaluated and polymer stability examined. Polymer hydrolytic degradation was investigated under physiological conditions to determine kojic acid-based poly(carbonate-ester's) and polyester's release profile and degradation media bioactivity assessed against identical concentrations of free kojic acid.

Materials and Methods

Materials.

1 N hydrochloric acid (HCl), polytetrafluoroethylene (PTFE), and poly(vinylidine fluoride) (PVDF) syringe filters, and Wheaton glass scintillation vials were purchased from Fisher Scientific (Fair Lawn, N.J.). Kojic Acid and Azelaic acid were acquired from Acros Organics (Morris Plains, N.J.). 1-Ethyl-3-(3-dimethylaminopropyl)carbodiimide (EDCI) was purchased from AK Scientific (Union City, Calif.). P-methoxybenzyl chloride was obtained from TCI (Portland, Oreg.). All other reagents, solvents, and fine chemicals were purchased from Aldrich (Milwaukee, Wis.) and used as received.

$^1$H and $^{13}$C NMR and FT-IR Spectroscopies.

Varian 400 or 500 MHz spectrometers were used to record proton ($^1$H) and carbon ($^{13}$C) nuclear magnetic resonance (NMR) spectra using deuterated chloroform (CDCl$_3$) with tetramethylsilane as an internal reference or deuterated dimethyl sulfoxide (DMSO-d$_6$) as solvent and internal reference. Fourier transform infrared (FT-IR) spectra were obtained using a Thermo Nicolet/Avatar 360 spectrometer, with samples (1-3 wt %) ground and pressed with potassium bromide (KBr) into a disc using an IR pellet die (International Crystal Laboratories, Garfield, N.J.) or solvent casted via dichloromethane (DCM) to acquire a thin film on sodium chloride (NaCl) plates. Each spectrum was an average of 32 scans.

Molecular Weight.

Polymer precursors were analyzed via mass spectrometry (MS) to determine molecular weights. A Finnigan LCQ- DUO equipped with Xcalibur software and an adjustable atmospheric pressure ionization electrospray ion source (API-ESI Ion Source) was used with a pressure of $0.8 \times 10^{-5}$ and 150° C. API temperature. Samples dissolved in methanol (<10 µg/mL) were injected via a glass syringe. Gel permeation chromatography (GPC) was used to determine polymer weight-averaged molecular weight ($M_w$) and polydispersity indices (PDI) using a Waters liquid chromatography system consisting of a Series 2414 refractive index detector, a 1515 isocratic high performance liquid chromatography (HPLC) pump, and a 717plus autosampler. Automation of the samples and processing of the data was performed using a Dell OptiPlex GX110 computer running Waters Breeze Version 3.20 software. Polymer samples were prepared for autoinjection by dissolving in DCM (10 mg/mL) and filtering through 0.45 µm PTFE syringe filters. Samples were resolved on a Jordi divinylbenzene mixed-bed GPC column (7.8×300 mm, Alltech Associates, Deerfield, Ill.) at 25° C., with DCM as the mobile phase at a flow rate of 1.0 mL/min. Molecular weights were calibrated relative to narrow polystyrene standards (Polymer Source Inc., Dorval, Canada).

Thermal Properties.

Differential scanning calorimetry (DSC) measurements were carried out on TA Instrument Q200 to determine melting ($T_m$) and glass transition ($T_g$) temperatures. Samples (4-6 mg) were heated under nitrogen atmosphere from −10° C. to 200° C. at a heating rate of 10° C./min and cooled to −10° C. at a rate of 10° C./min with a two-cycle minimum. TA Instruments Universal Analysis 2000 software, version 4.5A, was used to analyze the data. Thermogravimetric analysis (TGA) was utilized for determining decomposition temperatures ($T_d$) using a Perkin-Elmer Pyris 1 system with TAC 7/DX instrument controller and Perkin-Elmer Pyris software for data collection. Samples (5-10 mg) were heated under nitrogen atmosphere from 25° C. to 400° C. at a heating rate of 10° C./min. Decomposition temperatures were measured at the onset of thermal decomposition.

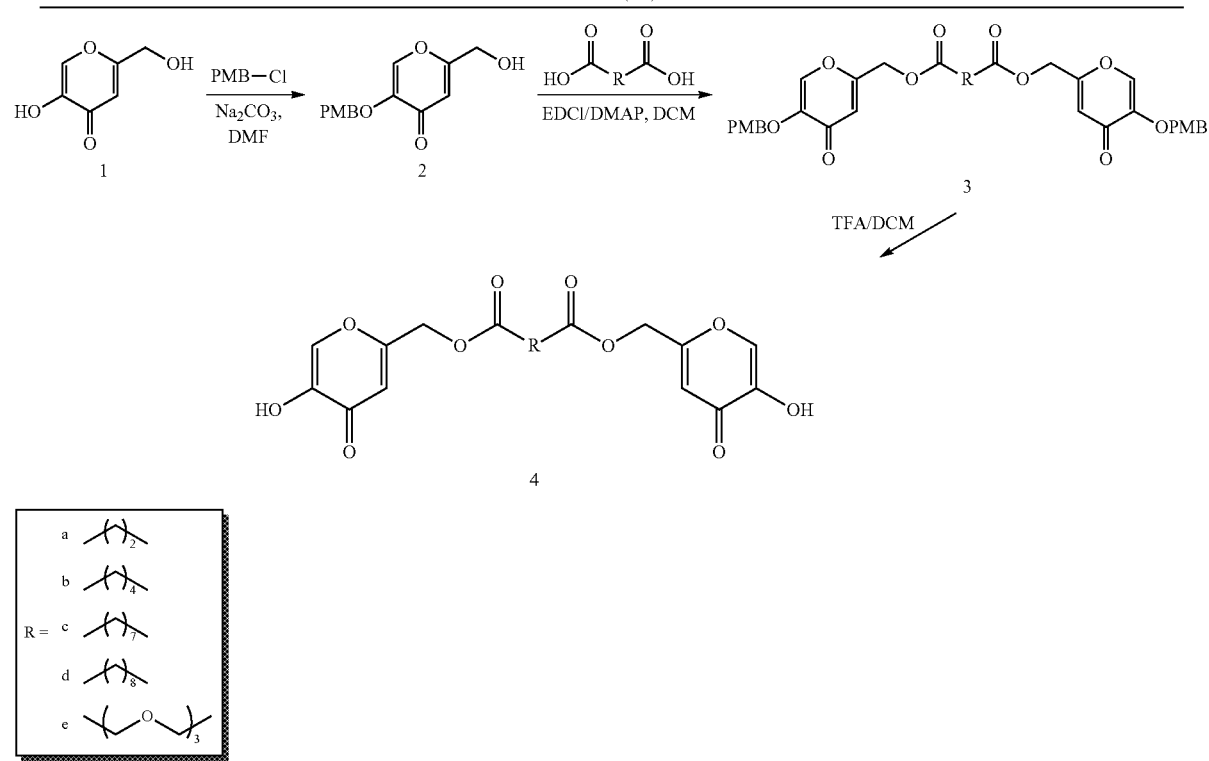

Scheme 2. KA-containing polymer precursors including PMB-KA (2), PMB-KA Diesters (3) with varying linkers (a-e), and KA Dienols (4) with varying linkers (a-e).

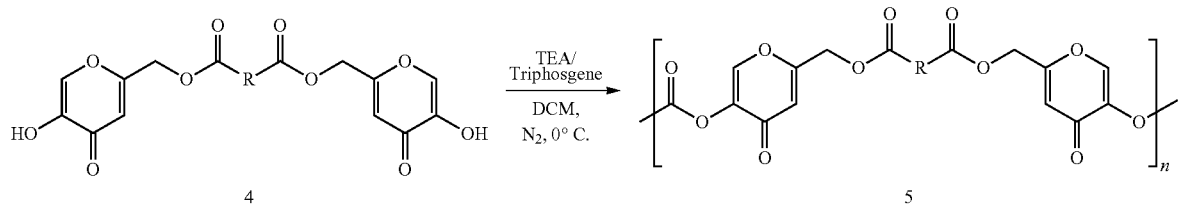

Scheme 3. Synthesis of KA Poly(carbonate-ester) (5), with various linkers (c-e), and KA Polyester (6), with various linkers (a-e).

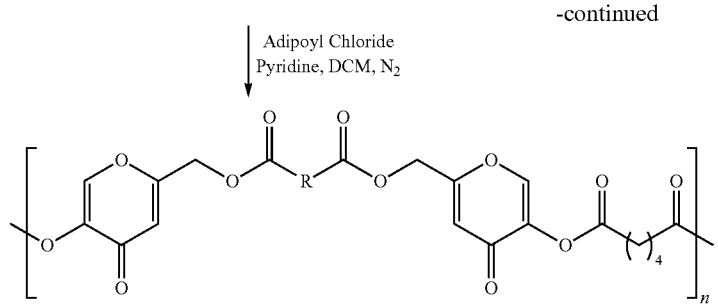

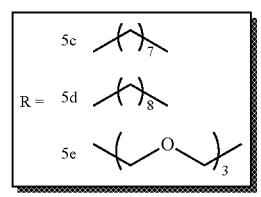

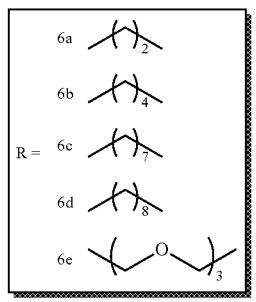

PMB-KA (2) Synthesis.

PMB-KA was synthesized utilizing a modified literature procedure (Chen, et al., *Med. Chem. Res.* 2013, 22, 995-1003). KA (1, 1 eq) was dissolved in 50 mL anhydrous dimethylformamide (DMF) under nitrogen. Anhydrous sodium carbonate ($Na_2CO_3$, 2.1 eq) and para-methoxybenzyl chloride (PMB-Cl, 1.05 eq) were added and the reaction flask, equipped with a reflux condenser and heated to 50° C. Thin layer chromatography (TLC, ethyl acetate eluent) was used to monitor the reaction progress. Following KA consumption the reaction was cooled to room temperature and solvent removed in vacuo. The resulting beige powder was triturated in 200 mL deionized (DI) water for 30 minutes and subsequently filtered. The residue was dried under vacuum overnight to acquire pure 2.

Yield: 77% (off-white powder). $^1$H-NMR (400 MHz, DMSO-$_{d6}$): δ 8.13 (s, 1H, Ar—H), 7.32 (d, 2H, Ar—H), 6.93 (d, 2H, Ar—H), 6.29 (s, 1H, Ar—H), 5.65 (t, 1H, —OH), 4.84 (s, 2H, —$CH_2$), 4.27 (d, 2H, —$CH_2$), 3.74 (s, 3H, —$CH_3$). $^{13}$C-NMR (DMSO-$_{d6}$): δ 173.7 (C), 168.4 (C), 159.7 (C), 147.0 (C), 141.6 (C), 130.5 (2C), 128.5 (C), 114.3 (2C), 111.6 (C), 70.8 (C), 59.8 (C), 55.6 (C). IR (KBr, cm$^{-1}$): 3311 (OH, alcohol), 1652 and 1617 (C=C).

PMB-KA Diester (3) Synthesis.

PMB-KA (2, 2 eq), Diacid (1 eq), and 4-dimethylaminopyridine (DMAP, 2.2 eq) were dissolved in 20 mL anhydrous DCM to which EDCI (3 eq) was added. TLC (ethyl acetate eluent) was used to monitor reaction progress. Following PMB-KA consumption, the reaction mixture was diluted with DCM (80 mL) and washed with 10% potassium bisulfate (3×100 mL) and saturated sodium bicarbonate (3×100 mL). The organic layer was collected, dried over $MgSO_4$, isolated via vacuum filtration, and concentrated in vacuo to acquire pure 3.

PMB-KA (Succinic) Diester (3a).

Succinic acid was used as the diacid. Yield: 86% (white powder). $^1$H NMR (400 MHz, DMSO-$_{d6}$): δ 8.19 (s, 2H, Ar—H), 7.32 (d, 4H, Ar—H), 6.93 (d, 4H, Ar—H), 6.43 (s, 2H, Ar—H), 4.95 (s, 4H, $CH_2$), 4.83 (s, 4H, $CH_2$), 3.74 (s, 6H, $OCH_3$), 2.69 (2, 4H, $CH_2$). $^{13}$C NMR (CDCl$_3$): δ 174.4 (2C), 172.0 (2C), 161.3 (2C), 159.8 (2C), 147.2 (2C), 141.8 (4C), 129.6 (2C), 127.7 (2C), 114.2 (4C), 114.1 (2C), 71.8 (2C), 61.0 (2C), 55.3 (2C) 33.6 (2C), 24.1 (2C). IR (NaCl, cm$^{-1}$): 1728 (C=O, ketone and ester), 1651 and 1618 (C=C).

PMB-KA (Adipic) Diester (3b).

Adipic acid was used as the diacid. Yield: 87% (white powder). $^1$H-NMR (500 MHz, CDCl$_3$): δ 7.54 (s, 2H, Ar—H), 7.31 (d, 4H, Ar—H), 6.90 (d, 4H, Ar—H), 6.41 (s, 2H, Ar—H), 5.01 (s, 4H, $CH_2$), 4.88 (s, 4H, $CH_2$), 3.79 (s, 6H, $OCH_3$), 2.42 (t, 4H, $CH_2$), 1.70 (t, 4H, $CH_2$). $^{13}$C NMR (CDCl$_3$): δ 174.4 (2C), 171.0 (2C), 161.0 (2C), 159.8 (2C), 147.1 (2C), 141.7 (4C), 129.6 (2C), 127.6 (2C), 114.3 (4C), 114.1 (2C), 71.7 (2C), 61.4 (2C), 55.3 (2C) 28.5 (2C). IR (NaCl, cm$^{-1}$): 1725 (C=O, ketone and ester), 1651 and 1621 (C=C).

PMB-KA (azelaic) Diester (3c).

Azelaic acid was used as the diacid. Yield: 95% (white powder). $^1$H-NMR (400 MHz, CDCl$_3$): δ 7.51 (s, 2H, Ar—H), 7.29 (d, 4H, Ar—H), 6.87 (d, 4H, Ar—H), 6.39 (s, 2H, Ar—H), 4.98 (s, 4H, $CH_2$), 4.85 (s, 4H, $CH_2$), 3.78 (s, 6H, $OCH_3$), 2.37 (t, 4H, $CH_2$), 1.62 (m, 4H, $CH_2$), 1.31 (m, 8H, $CH_2$). $^{13}$C-NMR (CDCl$_3$): δ 174.4 (2C), 172.5 (2C), 161.5 (2C), 159.8 (2C), 147.1 (2C), 141.7 (4C), 129.6 (2C), 129.6 (2C), 114.1 (4C), 114.0 (2C), 71.7 (2C), 60.9 (2C), 55.3 (2C), 33.8 (2C), 28.8 (3C), 24.6 (2C). IR (NaCl, cm$^{-1}$): 1747 (C=O, ester and ketone), 1656 and 1613 (C=C), and 1515 (C—C, aromatic).

PMB-KA (Sebacic) Diester (3d).

Sebacic acid was used as the diacid. Yield: 95% (white powder). $^1$H-NMR (400 MHz, CDCl$_3$): δ 7.51 (s, 2H, Ar—H), 7.30 (d, 4H, Ar—H), 6.87 (d, 4H, Ar—H), 6.40 (s, 2H, Ar—H), 4.99 (s, 4H, $CH_2$), 4.85 (s, 4H, $CH_2$), 3.79 (s, 6H, $OCH_3$), 2.37 (t, 4H, $CH_2$), 1.63 (m, 4H, $CH_2$), 1.30 (m, 8H, $CH_2$). $^{13}$C-NMR (CDCl$_3$): δ 174.4 (2C), 172.6 (2C), 161.6 (2C), 159.8 (2C), 147.1 (2C), 141.7 (4C), 129.6 (2C), 129.6 (2C), 114.1 (4C), 114.0 (2C), 71.7 (2C), 60.9 (2C), 55.3 (2C), 33.8 (2C), 28.9 (4C), 24.7 (C). IR (NaCl, cm$^{-1}$): 1732 (C=O, ester and ketone), 1651 and 1621 (C=C), and 1519 (C—C, aromatic).

PMB-KA (Tetraglycolic) Diester (3e).

3,6,9-trioxaundecanedioic acid was used as the diacid. The crude product was further purified by preabsorbing onto silica gel and performing flash chromatography using 100:0→60:40 ethyl acetate:acetone gradient. Yield: 43% (white powder). $^1$H-NMR (400 MHz, CDCl$_3$): δ 7.50 (a, 2H, Ar—H), 7.25 (d, 4H, Ar—H), 6.82 (d, 4H, Ar—H), 6.37 (s, 2H, Ar—H), 4.92 (s, 4H, CH$_2$), 4.88 (s, 4H, CH$_2$), 4.19 (s, 6H, CH$_3$), 3.73 (s, 4H, CH$_2$), 3.67 (m, 4H, CH$_2$), 3.64 (m, 4H, CH$_2$). $^{13}$C-NMR (CDCl$_3$): δ 174.3 (2C), 169.5 (2C), 160.8 (2C), 159.8 (2C), 147.8 (2C), 141.7 (4C), 129.6 (2C), 127.6 (2C), 114.4 (4C), 114.1 (2C), 71.7 (2C), 71.1 (2C), 70.6 (2C), 68.3 (2C), 61.2 (2C), 55.3 (C). IR (NaCl, cm$^{-1}$): 1765 (C=O, ester and ketone), 1651 and 1614 (C=C), and 1515 (C—C, aromatic).

KA Dienol (4) Synthesis.

Compound 3 (1 eq) was dissolved in anhydrous DCM (25 mL), and anhydrous trifluoroacetic acid (TFA, 10 eq) added (Chen, et al., Med. Chem. Res. 2013, 22, 995-1003). TLC (ethyl acetate eluent) was used to monitor reaction progress. Following 3 consumption, solvent was removed in vacuo and the resulting residue was triturated with ethyl acetate (25 mL), isolated via vacuum filtration, and dried in vacuo for 24 hours.

KA (succinic) Dienol (4a).

Yield: 95% (white powder). $^1$H-NMR (400 MHz, DMSO-$_{d6}$): δ 9.23 (bs, 2H, —OH), 8.06 (s, 2H, Ar—H), 6.45 (s, 2H, Ar—H), 4.95 (s, 4H, CH$_2$), 2.69 (s, 4H, CH$_2$). $^{13}$C-NMR (DMSO-$_{d6}$): δ 174.1 (2C) 171.8 (2C), 161.9 (2C), 146.5 (2C), 140.3 (2C), 112.9 (2C), 61.9 (2C), 28.8 (2C). MS: m/z=365.3 [M-1]

KA (adipic) Dienol (4b).

Yield: 95% (white powder). $^1$H-NMR (400 MHz, DMSO-$_{d6}$): δ 9.24 (bs, 2H, —OH), 8.09 (s, 2H, Ar—H), 6.47 (s, 2H, Ar—H), 4.96 (s, 4H, CH$_2$), 2.44 (t, 4H, CH$_2$), 1.58 (t, 4H, CH$_2$). $^{13}$C-NMR (DMSO-$_{d6}$): δ 174.1 (2C) 172.6 (2C), 162.0 (2C), 146.5 (2C), 140.3 (2C), 112.9 (2C), 61.7 (2C), 33.2 (2C), 24.1 (2C). MS: m/z=393.1 [M-1].

KA (Azelaic) Dienol (4c).

Yield: 92% (off-white powder). $^1$H-NMR (400 MHz, DMSO-$_{d6}$): δ 9.20 (bs, 2H, —OH), 8.06 (s, 2H, Ar—H), 6.42 (s, 2H, Ar—H), 4.93 (s, 4H, CH$_2$), 2.37 (t, 4H, CH$_2$), 1.50 (m, 4H, CH$_2$), 1.24 (m, 6H, CH$_2$). $^{13}$C-NMR (DMSO-$_{d6}$): δ 176.3 (2C), 174.9 (2C), 164.3 (2C), 148.7 (2C), 142.5 (2C), 115.1 (2C), 63.8 (2C), 35.7 (2C), 30.8 (3C), 26.7 (2C). IR (KBr, cm$^{-1}$): 3246 (OH, enol), 1746 (C=O, ester), 1732 (C=O, ketone), 1656 and 1633 (C=C). MS: m/z=435.4 [M-1].

KA (sebacic) Dienol (4d).

Yield: 89% (off-white powder). $^1$H-NMR (500 MHz, DMSO-d$_6$): δ 9.21 (s, 2H, —OH), 8.06 (s, 2H, Ar—H), 6.42 (s, 2H, Ar—H), 4.93 (s, 4H, CH$_2$), 2.36 (t, 2H, CH$_2$), 1.51 (m, 2H, J=16 Hz, R—CH=CH—R), 1.22 (s, 4H, CH$_2$), 3.84 (s, 6H, OCH$_3$). $^{13}$C-NMR (DMSO-$_{d6}$): δ 176.2 (2C), 174.9 (2C), 164.3 (2C), 148.7 (2C), 142.5 (2C), 142.4 (2C), 115.1 (2C), 63.7 (2C), 35.7 (2C), 31.1 (2C), 30.9 (2C), 26.9 (2C). IR (KBr, cm$^{-1}$): 3265 (OH, enol), 1748 (C=O, ester), 1729 (C=O, ketone), 1646 and 1622 (C=C). MS: m/z=449.4 [M-1].

KA (Tetraglycolic) Dienol (4e).

Yield: 97% (white powder). $^1$H-NMR (500 MHz, DMSO-d$_6$): δ 9.22 (s, 2H, COOH), 8.07 (d, 2H, 16 Hz, R—CH=CH—R), 6.48 (s, 2H, Ar—H), 4.99 (d, 2H, J=8 Hz, Ar—H), 4.23 (d, 2H, J=8 Hz, Ar—H), 3.59 (d, 2H, J=16 Hz, R—CH=CH—R), 3.53 (s, 4H, CH$_2$). $^{13}$C-NMR (DMSO-d$_6$): δ 174.1 (2C), 170.1 (2C), 161.7 (2C), 146.5 (2C), 140.4 (2C), 113.1 (2C), 70.5 (2C), 70.1 (2C), 67.9 (2C), 61.8 (2C). IR (KBr, cm$^{-1}$): 3261 (OH, enol), 1745 (C=O, ester), 1739 (C=O, ketone), 1644 and 1620 (C=C). MS: m/z=469.0 [M-1].

KA Poly(carbonate-ester) (5) Synthesis.

Polymer (5) was prepared using a modified solution polymerization (Scheme 3) (Schmeltzer, et al., J. Biomater. Sci. Polym. Ed. 2008, 19, (10), 1295-306). In brief, 4 (1 eq) was dissolved in anhydrous DCM (20 mL) under argon and triethylamine (TEA, 4.4 eq) added as a proton acceptor. The reaction mixture was cooled to 0° C., after which triphosgene (1 eq) dissolved in anhydrous DCM (5 mL) was added drop-wise (10 mL/h). The reaction was allowed to stir at 0° C. until CO$_2$ evolution ceased (ca. 4 h). The reaction mixture was poured over chilled diethyl ether (400 mL) and the precipitate isolated via vacuum filtration. The residue was dissolved in anhydrous DCM, washed with acidic water (1×250 mL), dried over MgSO$_4$, concentrated to ~10 mL, and precipitated with an excess of chilled diethyl ether (400 mL). Polymer 5 was isolated via vacuum filtration and dried in vacuo at room temperature.

KA (Azelaic) Polymer (5c).

Yield: 60% (beige powder). $^1$H-NMR (400 MHz, CDCl$_3$): δ 8.17 (s, 2H, Ar—H), 6.52 (s, 2H, Ar—H), 4.95 (s, 4H, —CH$_2$), 2.41 (t, 4H, —CH$_2$), 1.66 (bm, 4H, —CH$_2$), 1.35 (b, 6H, —CH$_2$). $^{13}$C-NMR (CDCl$_3$): δ 172.5 (2C), 171.5 (2C), 163.1 (2C), 148.9 (2C), 148.5 (2C), 141.4 (2C), 115.3 (2C), 60.9 (2C), 33.7 (2C), 28.7 (3C), 24.6 (2C). M$_w$=18.8 kDa, PDI=2.0. T$_g$=26° C., T$_d$=230° C.

KA (sebacic) Polymer (5d).

Yield: 54% (beige powder). $^1$H-NMR (400 MHz, CDCl$_3$): δ 8.14 (s, 2H, Ar—H), 6.52 (s, 2H, Ar—H), 4.95 (s, 4H, CH$_2$), 2.41 (t, 4H, CH$_2$), 1.66 (m, 4H, CH$_2$), 1.32 (m, 8H, CH$_2$). (NaCl, cm$^{-1}$): 1796 (C=O, carbonate), 1743 (C=O, ester and ketone), 1673 and 1643 (C=C). M$_w$=18.0 kDa Da, PDI=1.8. T$_g$=15° C. T$_d$=208° C.

KA (Tetraglycolic) Polymer (5e).

Yield: 90% (light beige powder). $^1$H-NMR (500 MHz, CDCl$_3$): δ 8.16 (s, 2H, Ar—H), 6.54 (s, 2H, Ar—H), 4.99 (s, 4H, CH$_2$), 4.26 (b, 4H, CH$_2$), 3.73 (b, 4H, CH$_2$), 3.67 (b, 4H, CH$_2$). M$_w$=7.2 kDa, PDI=1.1. T$_g$=32° C. T$_d$=251° C.

KA Polyester (6) Synthesis.

Polymer (6) was prepared following Scheme 3. In brief, 4 (1 eq) was dissolved in anhydrous 4 mL DCM, unless noted otherwise, under argon and pyridine (2.2 eq) added. Diacyl chloride (1.05 eq), dissolved in 2 mL anhydrous DCM, was then added dropwise over 1 h. The reaction was monitored via GPC until M$_w$ growth ceased (~4 h). The reaction was quenched with 25 mL 1 N HCl and taken up into a separatory funnel. The organic layer was washed 2×50 mL 1 N HCl, 2×50 mL sat. NaHCO$_3$, dried over MgSO$_4$, and concentrated in vacuo. The polymer was further dried under vacuum overnight to attain 6.

KA (Succinic) Polymer (6a).

Dimethylformamide (DMF, 5 mL) used as solvent. Yield: % (white powder). $^1$H-NMR (400 MHz, CDCl$_3$): δ 7.92 (s, 2H, Ar—H), 6.41 (s, 2H, Ar—H), 4.94 (s, 4H, CH$_2$), 2.77 (s, 4H, CH$_2$), 2.64 (bm, 4H, CH$_2$), 1.86 (bm, 4H, CH$_2$). M$_w$=5.5 kDa, PDI=1.6.

KA (Adipic) Polymer (6b).

Dimethylformamide (DMF, 5 mL) used as solvent. Yield: % (white powder). $^1$H-NMR (400 MHz, DMSO-$_{d6}$): δ 8.52 (s, 2H, Ar—H), 6.59 (s, 2H, Ar—H), 5.02 (s, 4H, CH$_2$), 2.63 (t, 4H, CH$_2$), 2.46 (t, 4H, CH$_2$), 1.71 (t, 4H, CH$_2$), 1.59 (t, 4H, CH$_2$). M$_w$=4.2 kDa, PDI=1.9.

KA (Azelaic) Polymer (6c).

Yield: 96% (white powder). $^1$H-NMR (400 MHz, CDCl$_3$): δ 7.90 (s, 2H, Ar—H), 6.47 (s, 2H, Ar—H), 4.91 (s, 4H, CH$_2$), 2.65 (bm, 4H, CH$_2$), 2.39 (t, 4H, CH$_2$), 1.87 (bm, 4H, CH$_2$), 1.65 (bm, 4H, CH$_2$), 1.33 (bm, 6H, CH$_2$). M$_w$=9.2 kDa, PDI=1.3. T$_g$=4° C.

KA (Sebacic) Polymer (6d).

Yield: 71% (white powder). $^1$H-NMR (400 MHz, CDCl$_3$): δ 7.89 (s, 2H, Ar—H), 6.47 (s, 2H, Ar—H), 4.93 (s, 4H, CH$_2$), 2.65 (bm, 4H, CH$_2$), 2.40 (t, 4H, CH$_2$), 1.86 (bm, 4H, CH$_2$), 1.65 (bm, 4H, CH$_2$), 1.31 (bm, 8H, CH$_2$). M$_w$=9.0 kDa, PDI=1.4. T$_g$=−1° C.

KA (Tetraglycolic) Polymer (6e). 7 mL 5:2 anhydrous DCM:DMF was used as solvent Yield: 81% (white powder). $^1$H-NMR (400 MHz, CDCl$_3$): δ δ 7.91 (s, 2H, Ar—H), 6.50 (s, 2H, Ar—H), 5.00 (s, 4H, CH$_2$), 4.27 (s, 4H, CH$_2$), 3.76 (t, 4H, CH$_2$), 3.71 (t, 4H, CH$_2$), 2.65 (bm, 4H, CH$_2$), 1.85 (bm, 4H, CH$_2$). M$_w$=9.6 kDa, PDI=1.7. T$_g$=10° C.

Dienol (4) Log P Determination.

Log P, partitioning coefficient of respective compounds between a hydrophilic (aqueous) and lipophilic (oil) phase, studies were conducted to investigate the relative hydrophobicity of Dienols (4). Using HPLC equipped with an XTerra reverse-phase C$_{18}$ (RP18) 3.5 μm 4.6×150 mm column (Waters, Milford, Mass.) and Waters 2695 Separations Module, sample retention times were analyzed via a Waters 2487 Dual λ Absorbance Detector monitoring 254 and 270 nm. Mobile phases of HPLC grade methanol (MeOH) and 50 mM KH$_2$PO$_4$ with 1% formic acid in HPLC grade water were utilized at varying ratios (45:55→60:40) and run at 1 mL/min flow rate and 25° C. (Ayouni, et al., *Chromatographia* 2005, 62, (5-6), 251-255). All samples were first dissolved in DMSO and subsequently diluted with phosphate-buffer saline (PBS) to acquire 1% DMSO solutions and filtered through 0.22 μm PVDF syringe filters prior to autoinjection (20 μL).

Dienol retention factor (k) for each methanol concentration was calculated according to equation one, where t$_R$ and t$_0$ are the retention times of the Dienols and dead time, as determined by the injection of sodium nitrate (Ayouni, et al., *Chromatographia* 2005, 62, (5-6), 251-255), respectfully. From the obtained retention factors the k$_w$, retention factor at 100% buffer, was extrapolated. Hydroxybenzyl alcohol, benzyl alcohol, 2-phenylethanol, methylparaben, anisole, toluene, and thymol were used as reference samples and their retention times acquired. Using reference samples' published Log P$_{o,w}$ values (OECD Nuclear Energy Agency.; Organisation for Economic Co-operation and Development. In *OECD guidelines for the testing of chemicals* 117, Organisation for Economic Co-Operation and Development: Paris, 2004), a calibration curve was generated in which Log P$_{o,w}$ values were plotted on the y-axis whereas log k$_w$ values, obtained from the same method as above, were plotted on the x-axis (Ouimet, et al., *Biomacromolecules* 2015, 16, 2911-2919). Dienol Log P values were then calculated from the curve using equation 2.

$k_w = (t_R - t_0)/t_0$ \hfill Equation 1

Log $P$ = slope×log $k_w$ + y-intercept \hfill Equation 2

Relative Polymer Hydrophobicity.

Relative hydrophobicity of KA poly(carbonate-esters) was determined by measuring sessile-drop contact angles of deionized (DI) water on polymer discs using an automated Ramé-hart goniometer (Model 250, Netcong, N.J.) with DROPimage advanced software. Polymer discs were prepared by pressing finely ground polymer samples (50±5 mg) into 8 mm diameter×1 mm width discs in an IR pellet die (International Crystal Laboratories, Garfield, N.J.) with a bench-top hydraulic press (Carver model M, Wabash, Ind.) by applying a pressure of 10,000 psi for 5 mM at room temperature. Angle measurements were obtained in triplicate for each polymer and an average value acquired. Measurements were taken following equilibrium (~10 seconds).

In Vitro KA Release.

Figure 4A:
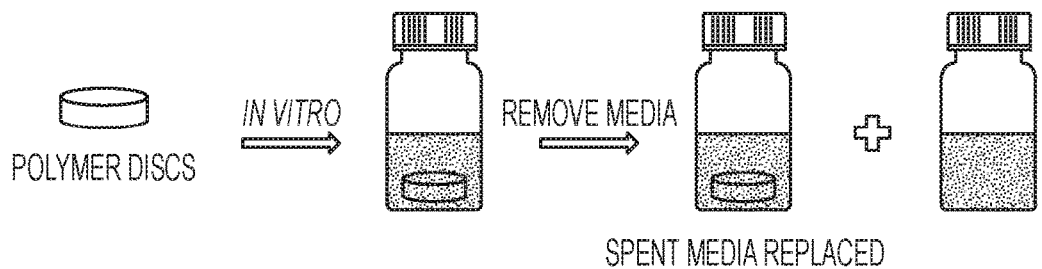
FIGS. 4A-C show kojic acid release via polymer degradation.
Figure 4B:
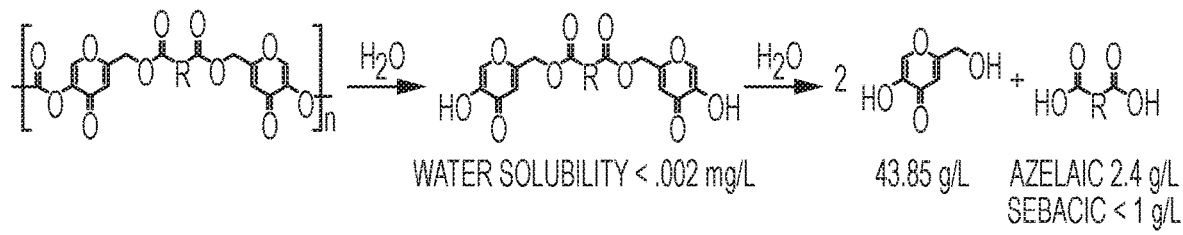
Figure 4C:
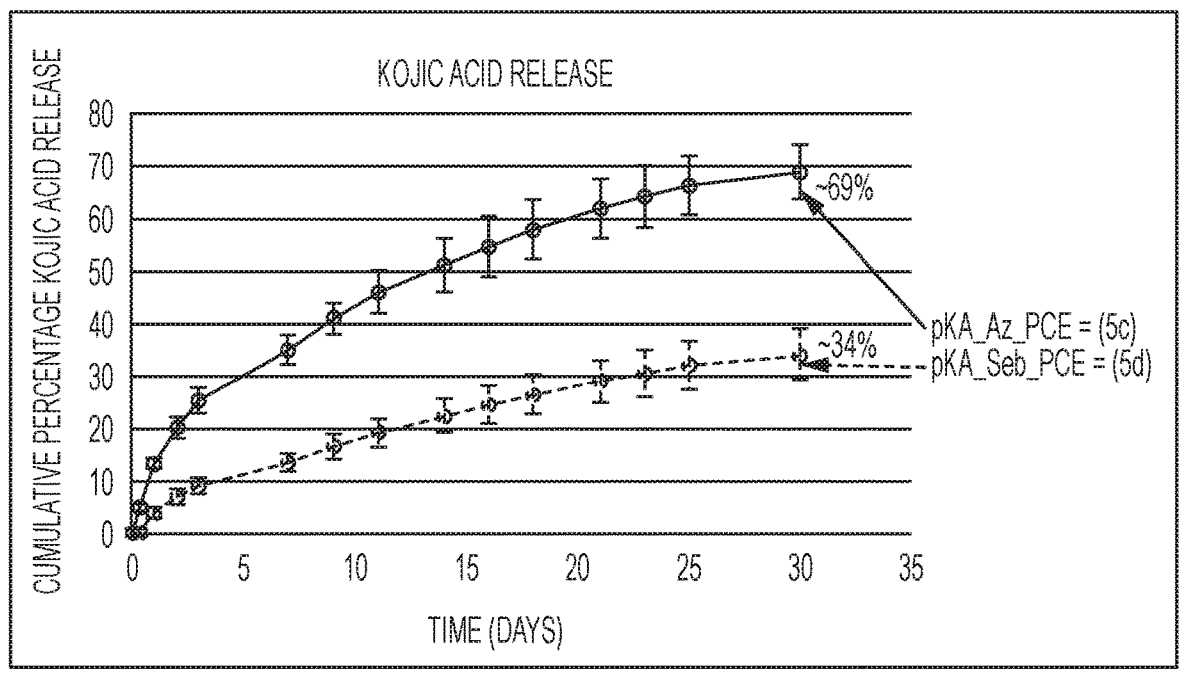
Figure 5:
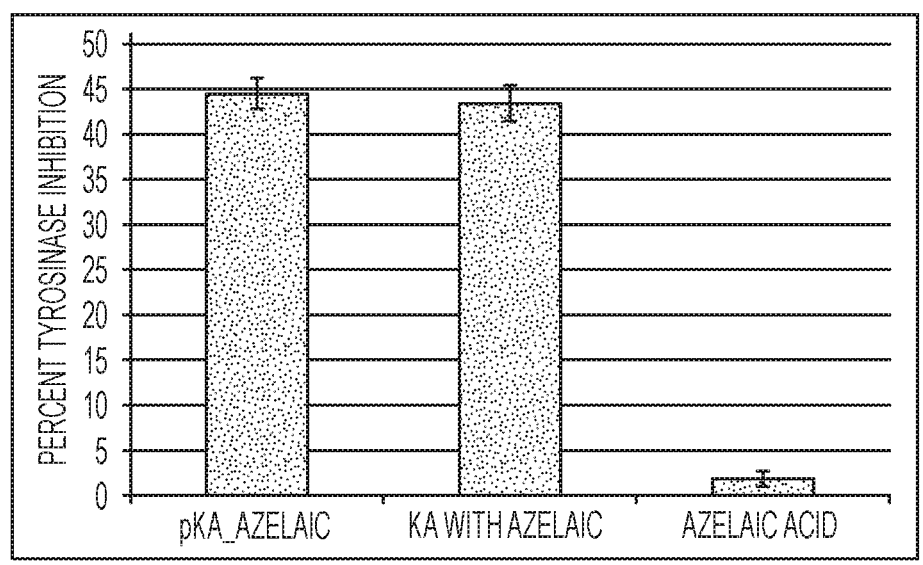
FIG. 5 shows day 10 degradation media tyrosinase inhibition activity of (5c), which has statistically similar activity when compared to its degradation products (KA and azelaic acid) at identical concentrations. Additionally, this data shows that the tyrosinase inhibition activity is predominately from KA as the concentration of azelaic acid is too low.

KA release from polymer discs (n=3, described above) was monitored in phosphate-buffer saline (PBS, pH=7.4), representing physiological conditions, and acetate buffer (pH=5.5), representing skin surface conditions (see, FIG. 4A). Polymer discs were incubated in 20 mL buffer in 20 mL Wheaton glass scintillation vials (Fisher Scientific, Fair Lawn, N.J.) at 37° C. with mild agitation (60 rpm) using a controlled environment incubator-shaker (New Brunswick Scientific Co., Edison, N.J.). To maintain sink conditions degradation media (20 mL) was removed at predetermined time-points and replaced with fresh buffer. Spent media was then examined via high-performance liquid chromatography (HPLC) with an ultraviolet-visible (UV-Vis) spectroscopy detector. The degradation products were analyzed and quantified via HPLC using an XTerra RP18 3.5 μm 4.6×150 mm column (Waters, Milford, Mass.) by a Waters 2695 Separations Module equipped with a Waters 2487 Dual 2 Absorbance Detector. Prior to autoinjection (20 μL) all samples were filtered through 0.22 μm PVDF syringe filters. A mobile phase of 10:90 acetonitrile and 50 mM KH$_2$PO$_4$ in HPLC grade water (Aldrich, Milwaukee, Wis.) with 1% formic acid at a flow rate of 1.0 mL/min was used to separate degradation media products at 25° C. Degradation media absorbance was monitored at 270 nm and KA release quantified based on previously established calibration curves of KA from known standard solutions (FIGS. 4A-C).

Mushroom Tyrosinase Inhibition Assay.

Small molecule dienols (4a-e) and degradation products' tyrosinase inhibition activity were assessed using a modified protocol and compared to that of free KA in vitro (Chen, et al., *Scientific reports* 2015, 5, 7995). Tyrosinase inhibition was evaluated by adding degradation media (25 μL) to 96-well plates containing phosphate buffer (80 μL, pH=6.8) and 125 μL substrate (0.5 mM L-DOPA) and incubated for 5 minutes at room temperature. A solution of mushroom tyrosinase (20 μL, 1250 U/mL) in phosphate buffer (pH=6.8) was then added and incubated an additional 5 minutes at room temperature. The amount of dopachrome produced was then recorded with a microplate reader (Coulter, Boulevard Brea, Calif.) at 475 nm.

Dienol (4a-e) tyrosinase inhibition activity was expressed as a function of its concentration and inhibitory concentration 50 (IC$_{50}$) values calculated and compared to KA (positive control). For degradation media, fresh KA solutions prepared at concentrations corresponding to day-10 HPLC data were analyzed identically to the aforementioned degradation media samples. Tyrosinase inhibition % reduction was calculated following Equation 3 where Abs$_{t0}$ is the negative control absorbance and Abs$_t$ is the sample (degradation media or KA) absorbance after 5 minutes. Abs$_{t0}$ values were determined by adding 25 μL to the 96-well plates in place of the samples and analyzing the resulting absorbance (λ=475 nm). All samples were corrected for background absorbance and performed in triplicate. Student's t-tests were performed to determine significant differences between free KA and KA degradation media tyrosinase inhibition (p<0.05).

$[(Abs_{t0} - Abs_t)/Abs_{t0}]*100$ \hfill Equation 3

Cytotoxicity.

In vitro cytocompatibility studies were performed by culturing 3T3 mouse fibroblasts in cell media (Dulbecco's Modified Eagle Medium supplemented with 10% Fetal Bovine Serum, 1% Penicillin Streptomycin, and 1% L-glutamate) containing the KA poly(carbonate-esters). Polymers (5a-5c, 6a-6e) and Dienols (4a-4e) were first sterilized under UV at λ=254 nm for 900 s (Spectronics Corporation, Westbury, N.Y.) and subsequently dissolved in DMSO to acquire a stock solution. The stock solution was then serial diluted with cell media. Cells were seeded in a 96-well plate at 2,000 cells/well in 100 media. Following incubation for 1 h, polymer-containing media in 1% DMSO, at concentrations capable of inhibiting tyrosinase (0.1 mg/mL, 0.01 mg/mL and 0.001 mg/mL) were added to allocated wells in a 96-well plate and incubated at 37° C. DMSO (1%) in cell media was used as a negative control.

Cell viability was determined using CellTiter 96® Aqueous One Solution Cell Proliferation Assay. After 24 h, 48 h, and 72 h incubation with polymers, 20 μL of (3-(4,5-dimethylthiazol-2-yl)-5-(3-carboxymethoxyphenyl)-2-(4-sulfophenyl)-2H-tetrazolium) (MTS) reagent was added to each well and further incubated for 4 h at 37° C. The absorbance was then recorded with a microplate reader (Coulter, Boulevard Brea, Calif.) at 490 nm.

Results

Synthesis and Characterization.

Poly(carbonate-esters) and polyesters comprised of KA and linear aliphatic and oxygen-containing diacids were successfully synthesized. Following previously published methods, PMB-KA (2) was prepared via a selective $S_N2$ reaction with PMB-Cl at the enolic site of KA (Chen, et al., *Med. Chem. Res.* 2013, 22, 995-1003). PMB-KA diesters (3) were subsequently synthesized via carbodiimide coupling using EDCI and DMAP. The diacids (succinic, adipic, azelaic, sebacic, and 3,6,9-trioxaundecanedioic acid) were separately reacted with PMB KA to acquire 3. The low purity of commercially available 3,6,9-trioxaundecanedioic acid (~70%) necessitated using column chromatography to further purify the resulting crude product. KA dienols (4) were obtained following a modified procedure described by Chen et al., in which the PMB-moiety was selectively deprotected using TFA (Chen, et al., *Med. Chem. Res.* 2013, 22, 995-1003). Successful synthesis of 2 was confirmed by the absence of the enolic proton and appearance of PMB aromatic (7.32 and 6.93 ppm), benzyl (4.84 ppm), and methoxy protons (3.74 ppm, FIG. 1) and the aromatic functionality in both $^{13}C$ NMR and FTIR spectra. Using 3c as an example, the structure was confirmed by the presence of linker methylene protons (2.37, 1.62, and 1.31 ppm, FIG. 1) in $^1H$ NMR and the ester functionality in both $^{13}C$ NMR and FTIR spectra. Subsequent deprotection to acquire 4 was validated by the absence of the PMB peaks (FIG. 1) in $^1H$ NMR. MS corroborated the mass of polymer precursors (3 and 4).

Following isolation and characterization of 4, KA poly(carbonate-esters) were synthesized utilizing a modified solution polymerization with TEA as a proton acceptor and triphosgene as a dehydrochlorination coupling reagent (Schmeltzer, et al., *J. Biomater. Sci. Polym. Ed.* 2008, 19, (10), 1295-1309). In initial trials pyridine was utilized in place of TEA owing to its use in triphosgene-mediated solution polymerization to acquire polycarbonates (Shpaisman, et al., *Biomacromolecules* 2012, 13, (8), 2279-86), however, it was found to reduce $M_w$ and yield. Furthermore, polymerization attempts with 4a and 4b resulted in insoluble systems and were not further characterized. Dienol polymerization was confirmed by the downfield shift in olefin peaks of KA (FIG. 1) and by the manifestation of the carbonate bond in $^{13}C$ NMR and FTIR spectrums. KA polyesters were also synthesized utilizing a modified procedure in which pyridine facilitated O-acylation of adipoyl chloride to acquire 6 (Pion, et al., *Macromolecular Chemistry and Physics* 2014, 215, (5), 431-439). Using 6d as an example, successful polymerization was indicated by the absence of the enolic proton and the appearance of new methylene peaks at 2.65 and 1.86 ppm.

KA poly(carbonate-esters) possessed molecular weights ranging from 7.2 to 18.8 kDa with aliphatic linked KA Dienols producing higher molecular weight polymers (5a-b). Additionally, the linker composition and length was found to influence $T_g$, with heteroatom containing (5c) possessing the highest $T_g$ and decreasing aliphatic linker length culminating in a higher $T_g$. It is hypothesized that the former is due to the shorter C—O bond relative to C—C bond reducing the polymer flexibility, whereas the latter is consistent with literature (Prudencio, et al., *Macromol. Biosci.* 2016, 16(2), 214-22; Prudencio, et al., *Macromolecules* 2005, 38, (16), 6895-6900). KA polyesters consistently displayed lower M, when compared to KA poly(carbonate-ester) counterparts, with $M_w$ ranging from 4.2-9.6 kDa. As was expected, KA polyesters also possessed lower $T_g$s owing to the introduction of a more flexible aliphatic linkage.

Dienol (4) Log P Determination.

Dienol (4) Log P studies were conducted to both gain insight to water solubility, as 5c rapidly degrades when solubilized and 5a-b are sparingly soluble, and skin permeation candidacy as Log P can be utilized as an estimate of permeability. Thus, Dienol Log P values were extrapolated from an HPLC method to determine lipophilicity (OECD Nuclear Energy Agency.; Organisation for Economic Cooperation and Development. In *OECD guidelines for the testing of chemicals* 117, Organisation for Economic Co-Operation and Development: Paris, 2004). Retention factors (k) were calculated according to equation 1 for each concentration of MeOH and $k_w$ values extrapolated based off the retention times (Table 1).

TABLE 1

Calculated Log P values for dienols (4a-e) to elucidate lipophilicity

| Sample | Calculated $k_w$ | Calculated Log P Values |
| --- | --- | --- |
| 4a | 0.806 | 0.353 |
| 4b | 2.40 | 1.17 |
| 4c | 16.0 | 2.59 |
| 4d | 31.6 | 3.10 |
| 4e | 0.688 | 0.235 |

The calculated log P values in Table 1 follow the trend 4e<4a<4b<4c<4d. As expected, 4e was the most hydrophilic dienol presumably due to the increase in oxygen content as similar trends have been observed (Ouimet, et al., *Biomacromolecules* 2015, 16, 2911-2919), while the remaining dienols followed a trend of increasing aliphatic content between the kojic moieties. All compounds possessed a Log P value greater than kojic acid itself, which has been reported as low as −1.11 and high as −0.66 (Rho, et al. *Bull. Korean Chem. Soc.* 2007, 28, (3), 471-473; Heng, et al. *Handbook of Cosmeceutical Excipients and Their Safeties*. Woodhead Publishing: New York, N.Y., 2014)

In Vitro KA Release.

KA poly(carbonate-ester) hydrolytic degradation was studied utilizing polymer discs to minimize formulation influence on KA release. Polymer discs were immersed in PBS under physiological conditions (pH=7.4, 37° C.) and polymer degradation investigated using HPLC, monitoring KA release. Degradation media KA concentration was quantified at each time-point based on standardized calibration curves.

KA poly(carbonate-esters) were found to hydrolytically degrade through the carbonate bond first, generating Dienol (4), which subsequently underwent further hydrolysis to release KA as confirmed by HPLC. While carbonate bonds are classically more robust and stable towards hydrolysis than esters, it is hypothesized that the enhanced stability of the enol leaving group and hydrophilicity of the surrounding KA moieties promoted faster hydrolytic degradation. Furthermore, upon initial hydrolysis at the carbonate site an unstable carbonic acid forms, which literature has shown to readily decarboxylate, releasing $CO_2$ and the enol. HPLC chromatograms displayed a peak at 2.23 min, corresponding to KA, while additional peaks were present at later retention times, representing other degradation products (i.e., mono-enols, dienols, etc.).

The release profile of KA poly(carbonate-esters) was found to be drastically influenced by the linker molecule. The water miscible, hydrophilic 3,6,9-trioxaundecanedioic acid linker of 5e promoted complete polymer degradation within three days, whereas aliphatic linked 5c and 5d released 69% and 34% of KA after 30 days (FIG. 4C). Although only differing by a methylene unit, 5c released KA considerably quicker than 5d. These results are presumed to be due to the enhanced hydrophilicity of 5c as corroborated by log P analysis. Moreover, Dienol log P trends were consistent with polymer release profiles with decreasing log P (increasing hydrophilicity) correlating to increased KA release rate. The KA release from 5c and 5d was also monitored and quantified over 30 days.

Mushroom Tyrosinase Inhibition Assay.

Both Dienol (4a-4e) and polymer degradation products were determined by a modified procedure using L-DOPA as a substrate (Chen, et al., *Scientific reports* 2015, 5, 7995). Polymer degradation products were found to possess similar tyrosinase inhibition activity as their free small molecule counterparts, using identical concentrations (as determined by HPLC). Interestingly, all Dienols (4a-4e) IC50 values were significantly more potent than kojic acid, most notably for compounds 4a-4c.

TABLE 2

IC50 values of Dienol compounds showing enhanced potency relative to kojic acid itself.

| Compound | IC50 (uM) | Ratio |
|---|---|---|
| 4a | 75.72 | 5.362 |
| 4b | 60.94 | 6.662 |
| 4c | 94.63 | 4.290 |
| 4d | 270.4 | 1.502 |
| 4e | 336.1 | 1.208 |
| Kojic Acid | 406.0 | 1 |

Cytotoxicity.

To ensure topical use of KA poly(carbonate-esters) was appropriate, cytotoxicity studies were conducted using 3T3 mouse fibroblasts. Cells were incubated in the presence of polymer-containing media at 0.1, 0.01, and 0.001 mg/mL, whereas DMSO-containing media was used as a control. These concentrations represent therapeutically relevant values based off KA $IC_{50}$ studies in literature (Neeley, et al., *International journal of molecular sciences* 2009, 10, (9), 3811-23). Studies were performed over a 72 h duration, monitoring cell viability every 24 h.

Figure 6:
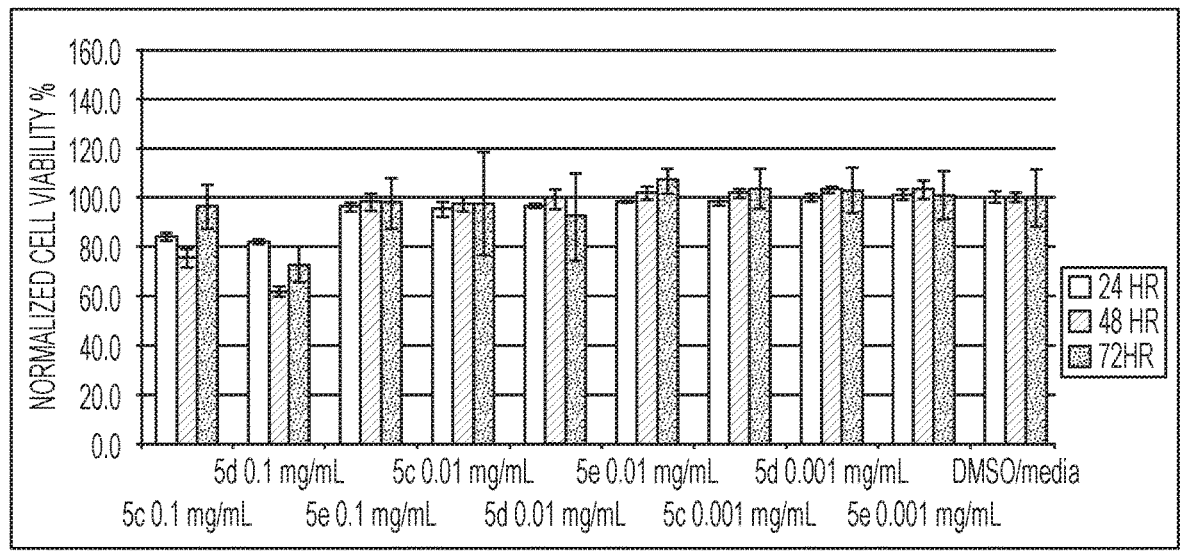
FIG. 6 shows KA poly(carbonate-ester) cytotoxicity following 24, 48, and 72 h in cell culture media with polymer concentrations of 0.1, 0.01, and 0.001 mg/mL. Within each grouping, 24 h is shown on the left, 48 h in the middle and 72 h on the right.

Collectively, all KA poly(carbonate-esters) were cyto-compatible—exhibiting no statistical difference in cell viability between polymer samples and DMSO control—at 0.01 mg/mL and 0.001 mg/mL over 72 hours (FIG. 6). At 0.1 mg/mL, 5e was found to be cytocompatible whereas 5c and 5d exhibited cytotoxicity. It is hypothesized that the increased hydrophilicity of 5c, as demonstrated by log P analysis, is responsible for the improved cytocompatibility.

Overall, all KA poly(carbonate-esters) were found to be cytocompatible at therapeutically relevant concentrations as determined by KA tyrosinase inhibition activity.

Figure 7:
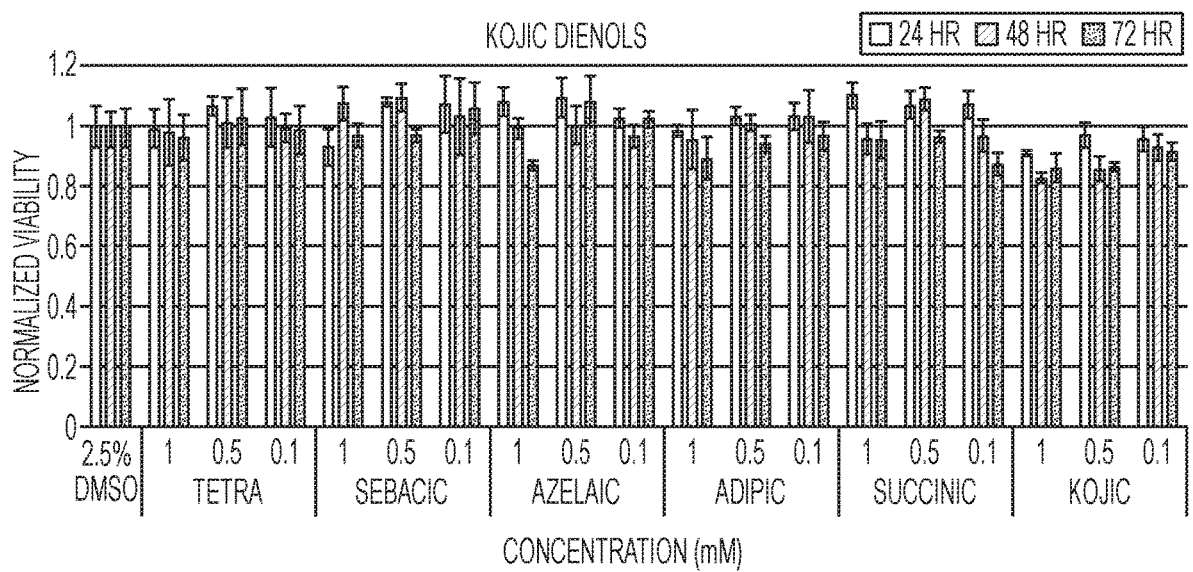
FIG. 7 shows the cytocompatibility profile of the monomers (4a-4e). Within each grouping, 24 h is shown on the left, 48 h in the middle and 72 h on the right.

As the dienols (4a-4e) displayed significantly better tyrosinase inhibition than kojic acid itself, their cytocompatibility was also investigated. All dienols were found to be cytocompatible well above their IC50 values (1000 μM) after 24 h whereas kojic acid slightly cytotoxic (FIG. 7). This provides an additional advantage of polymer 5 and 6 as both systems release their respective dienol, which all are more potent tyrosinase inhibitors and more cytocompatible.

Example 3. Evaluation of Polymers and Dienols Comprising Kojic Acid in Melanocytes The polymers and dienols described in Examples 1 and 2 may be further evaluated in melanocytes. Described below are two assays, which may be performed to evaluate to the polymers and compounds of the invention: MTT cytotoxicity assay and melanin assay.

Cytotoxicity Assay (MTT)

Aspirate media from the cells, add 1 mL of trypsin and incubate 1-3 min at RT until cells lift from plate. Collect the cells/trypsin, add contents to 15 mL centrifuge tube and spin at 180×g for 7 min. Remove supernatant and resuspend pellet in 4 mL media. Count cells using hemocytometer by combining 20 μL cell suspension with 20 μL trypan blue. Dilute cells to $2\times10^3$ cells/mL and plate 100 μL/well ($2\times10^4$ cells/well) in 96 well plate. After 24 h, replace media with treatments (51 wells total): 1) 5 samples in triplicate at 3 concentrations (45 wells); 2) no treatment control in triplicate (3 wells); and 3) kojic acid treatment control in triplicate (3 wells). Incubate cells with treatment for 24, 48 or 72 h. Prepare MTT stock solution (component A): add 1 mL of sterile PBS to one 5 mg vial of MTT and mix by vortexing (enough for 100 tests). The MTT stock solution may be stored at 4° C. for 4 weeks. Prepare component B solution: add 10 mL of 0.01 M HCl to one tube containing 1 g SDS (component B) and mix by inversion. The component B solution should be prepared immediately before use (enough for 100 tests). Remove media from cells, replace with 100 μL of fresh media. Add 100 μL of MTT stock solution (component A) to each well, incubate for 4 h at 37° C. Add 100 μL of SDS-HCl solution (component B), mix using pipette and incubate for 4 h at 37° C. Mix each sample using pipette and read absorbance using 570 nm using plate reader.

Melanin Assay

Plate cells at $5\times10^4$ cells/well in a 24 well plate (51 wells total): 1) 5 samples in triplicate at 3 concentrations (45 wells); 2) no treatment control (3 wells); 3) kojic acid control (3 wells). Incubate for 24 h at 37° C. Aspirate media and trypsinize cells with 100 μL of trypsin per well and incubate at RT for 1-3 mins, until cells lift from plates. Add 100 uL 10% FBS in DMEM to neutralize trypsin. Transfer lifted cells to microcentrifuge tubes and then wash wells with 50 uL 10% FBS in DMEM and add to tubes. Centrifuge at 180×g for 7 min. Heat 1N NaOH to 70° C. and dissolve cell pellets in 200 μL NaOH. Heat samples at 70° C. on heat block for 1 h. Centrifuge tubes at 10,000×g for 10 min. Transfer 100 μL of supernatant to 96 well plate and read absorbance at 405 nm.

All publications, patents, and patent documents including the documents identified below are incorporated by reference herein, as though individually incorporated by reference.

Erdmann, L. et al. *Biomaterials*, 21, 1941-1946 (2000)
Schmeltzer, R. et al. *Polym. Bull*, 49, 441-448 (2003)
Prudencio, Almudena. et al. *Macromolecules*, 8, 6895-6901 (2005)
Aytemir, Karakaya. et al. *Medicinal Chemistry and Drug Design*, 1-21 (2012)

Balasubramanian, A. et al. *Journal of Applied Packaging Research*, 3, 193-221 (2009)

Mounia, Oussalah. et al J. *Agric. Food Chem* 52 5598-5605 (2004)

Coma, V. et al. *Meat Science* 78 90-103 (2008)

The invention has been described with reference to various specific and preferred embodiments and techniques. However, it should be understood that many variations and modifications may be made while remaining within the spirit and scope of the invention.

What is claimed is:

1. A polymer having a backbone that comprises one or more units of formula (I):

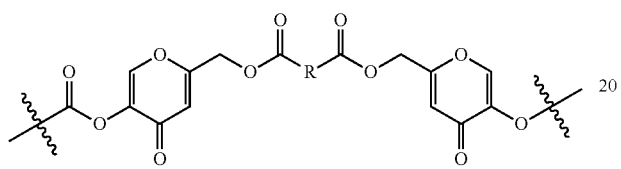

wherein:
R is a divalent, branched or unbranched, saturated or unsaturated, hydrocarbon chain, having from 1 to 25 carbon atoms, wherein one or more of the carbon atoms is optionally replaced by (—O—) or (—$NR_a$—), wherein the chain is optionally substituted on carbon with one or more substituents selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy, and wherein $R_a$ is H or $C_1$-$C_6$ alkyl.

2. The polymer of claim 1, which has a backbone that comprises formula 5:

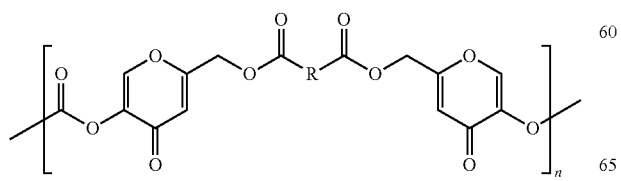

wherein:
R is a divalent, branched or unbranched, saturated or unsaturated, hydrocarbon chain, having from 1 to 25 carbon atoms, wherein one or more of the carbon atoms is optionally replaced by (—O—) or (—$NR_a$—), wherein the chain is optionally substituted on carbon with one or more substituents selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy;
$R_a$ is H or $C_1$-$C_6$ alkyl; and
n is an integer from 2 to 500 inclusive.

3. The polymer of claim 1, wherein R is a divalent hydrocarbon chain having 2, 4, 7 or 8 carbon atoms or wherein R is —($CH_2OCH_2$)$_3$—.

4. A method for preparing a polymer as described in claim 2:
comprising polymerizing a corresponding diol of formula 4:

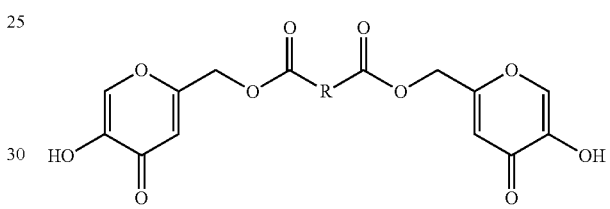

to provide the polymer.

5. A polymer having a backbone that comprises one or more units of formula (II):

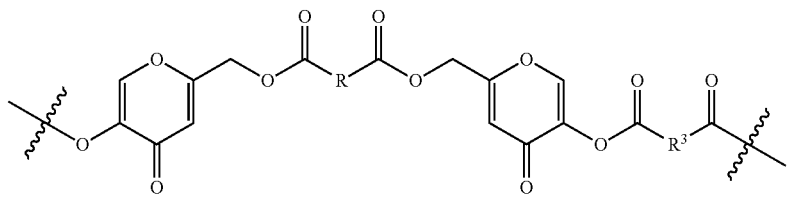

wherein:
R and $R^3$ are each independently a divalent, branched or unbranched, saturated or unsaturated, hydrocarbon chain, having from 1 to 25 carbon atoms, wherein one or more of the carbon atoms is optionally replaced by (—O—) or (—$NR_a$—), wherein the chain is optionally substituted on carbon with one or more substituents selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy, and $R_a$ is H or $C_1$-$C_6$ alkyl.

6. The polymer of claim 5, which has a backbone that comprises formula 6:

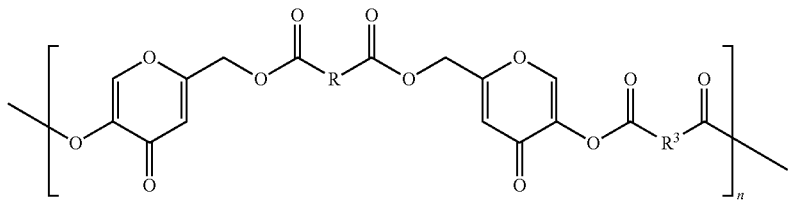

wherein:
R and $R^3$ are each independently a divalent, branched or unbranched, saturated or unsaturated, hydrocarbon chain, having from 1 to 25 carbon atoms, wherein one or more of the carbon atoms is optionally replaced by (—O—) or (—$NR_a$—), wherein the chain is optionally substituted on carbon with one or more substituents selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy;

$R_a$ is H or $C_1$-$C_6$ alkyl; and n is an integer from 2 to 500 inclusive.

7. The polymer of claim 5 wherein R is a divalent hydrocarbon chain having 2, 4, 7 or 8 carbon atoms or wherein R is —($CH_2OCH_2$)$_3$—.

8. The polymer of claim 5 wherein $R^3$ is a divalent hydrocarbon chain having 4 carbon atoms.

9. A composition comprising a polymer as described in claim 1 and a pharmaceutically acceptable carrier.

10. A cosmetic formulation comprising a polymer as described in claim 1 and an acceptable carrier.

11. A method for preparing a polymer as described in claim 6:
comprising reacting a corresponding diol of formula 4:

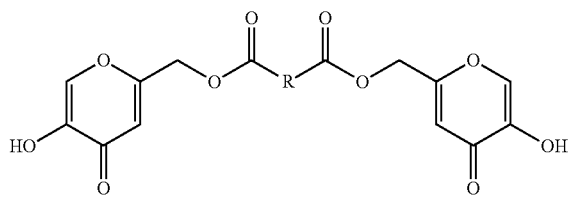

with a corresponding diacid chloride of formula:

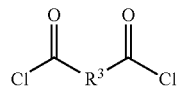

to provide the polymer.

12. The polymer of claim 3, wherein R is —($CH_2OCH_2$)$_3$—.

13. A composition comprising a polymer as described in claim 5 and a pharmaceutically acceptable carrier.

14. A cosmetic formulation comprising a polymer as described in claim 5 and an acceptable carrier.

15. The polymer of claim 1, wherein R is a divalent, branched or unbranched, saturated or unsaturated, hydrocarbon chain, having from 3 to 15 carbon atoms, wherein one or more of the carbon atoms is optionally replaced by (—O—) or (—$NR_a$—), and wherein $R_a$ is H or $C_1$-$C_6$ alkyl.

16. The polymer of claim 5, wherein R is a divalent, branched or unbranched, saturated or unsaturated, hydrocarbon chain, having from 3 to 15 carbon atoms, wherein one or more of the carbon atoms is optionally replaced by (—O—) or (—$NR_a$—), and wherein $R_a$ is H or $C_1$-$C_6$ alkyl.

* * * * *